US007815913B2

(12) United States Patent
Masarapu et al.

(10) Patent No.: US 7,815,913 B2
(45) Date of Patent: Oct. 19, 2010

(54) CHIMERIC TYMOVIRUS-LIKE PARTICLES AND PROCESS THEREOF

(75) Inventors: Hema Masarapu, Hyderabad (IN); Singanallur Balasubramanian Nagendrakumar, Hyderabad (IN); Dorairajan Thiagarajan, Hyderabad (IN); Villuppanoor Alwar Srinivasan, Hyderabad (IN)

(73) Assignee: Indian Immunologicals Limited (IN)

( * ) Notice: Subject to any disclaimer, the term of this patent is extended or adjusted under 35 U.S.C. 154(b) by 0 days.

(21) Appl. No.: 12/211,523

(22) Filed: Sep. 16, 2008

(65) Prior Publication Data

US 2009/0087861 A1  Apr. 2, 2009

Related U.S. Application Data

(63) Continuation of application No. PCT/IN2006/000342, filed on Sep. 11, 2006.

(30) Foreign Application Priority Data

Mar. 17, 2006 (IN) .......................... 486/CHE/2006

(51) Int. Cl.
*A61K 39/12* (2006.01)
*A61K 39/00* (2006.01)
*A61K 39/135* (2006.01)

(52) U.S. Cl. ............... 424/199.1; 424/192.1; 424/216.1
(58) Field of Classification Search ...................... None
See application file for complete search history.

(56) References Cited

U.S. PATENT DOCUMENTS

2007/0160628 A1* 7/2007 Birkett et al. ............ 424/204.1

OTHER PUBLICATIONS

Mira Sastri et al.; Identification of a Discrete Intermediate in the Assembly/Disassembly of Physalis Mottle Tymovirus through Mutational Analysis; publication; 1999; 14 pages, pp. 905-918; vol. 289; J. Mol. Biol. (1999); Academic Press.
Ramakrishnan Usha et al.; Expression of an Animal Virus Antigenic Site on the Surface of a Plant Virus Particle; publication; 1993; 9 pages, pp. 366-374; vol. 197; Virology; Academic Press, Inc.
J. Johnson et al.; Presentation of Heterologous Peptides on Plant Viruses: Genetics, Structure, and Function; publication; 1997; 21 pages, pp. 67-86 (and copyright notice); vol. 35; Annu. Rev. Phytopathol.; Annual Reviews Inc.
Wieslaw Niedbalski; Comparison of Three Elisa Kits for the Detection of Antibodies Against Foot-and-Mouth Disease Virus Non-Structural Proteins; publication; Dec. 10, 2004; 5 pages; pp. 147-151; vol. 49; Bull Vet Inst Pulawy.
Fred Brown; The history of research in foot-and-mouth disease; publication; 2003; 5 pages, pp. 3-7; vol. 91; Virus Research; Science Direct; Elsevier.
Wen-Bin Chung et al.; Differentiation of Foot-and-Mouth Disease Virus-Infected from Vaccinated Pigs by Enzyme-Linked Immunosorbent Assay Using Nonstructural Protein 3AB as the Antigen and Application to an Eradication Program; publication; Aug. 2002; 6 pages, pp. 2843-2848; vol. 40, No. 8; Journal of Clinical Microbiology; American Society for Microbiology.
Alfonso Clavijo et al.; Developments in diagnostic techniques for differentiating infection from vaccination in foot-and-mouth disease; publication; 2004; 14 pages, pp. 9-22; vol. 167; The Veterinary Journal; Science Direct; Elsevier.
Alfonso Clavijo et al.; Development and use of a biotinylated 3ABC recombinant protein in a solid-phase competitive ELISA for the detection of antibodies against foot-and-mouth disease virus; publication; 2004; 11 pages, pp. 217-227; vol. 120; Journal of Virological Methods; Science Direct; Elsevier.
M. De Diego et al.; The non-structural polyprotein 3ABC of foot-and-mouth disease virus as a diagnostic antigen in ELISA to differentiate infected from vaccinated cattle; publication; 1997; 13 pages, pp. 2021-2033; vol. 142; Archives of Virology; Springer-Verlag; Austria.
T.R. Doel; FMD vaccines; publication; 2003; 19 pages, pp. 81-99; vol. 91; Virus Research; Science Direct; Elsevier.
Liliane Grangeot-Keros et al.; Evaluation of a New Enzyme Immunoassay Based on Recombinant rubella Virus-Like Particles for Detection of Immunoglobulin M Antibodies to Rubella Virus; publication; Feb. 1997; 4 pages, pp. 398-401; vol. 35, No. 2; Journal of Clinical Microbiology; American Society for Microbiology.
Marvin J. Grubman et al.; Foot-and-Mouth Disease; publication; Apr. 2004; 29 pages, pp. 465-493; vol. 17, No. 2; Clinical Microbiology Reviews.
Minghang Guo et al.; Expression and Self-Assembly in Baculovirus of Porcine Enteric Calicivirus Capsids into Virus-Like Particles and Their Use in an Enzyme-Linked Immunosorbent Assay for Antibody Detection in Swine; publication; Apr. 2001; 7 pages, pp. 1487-1493; vol. 39, No. 4; Journal of Clinical Microbiology; American Society for Microbiology.
Bettina-Judith Höhlich et al.; Identification of Foot-and Mouth Disease Virus-Specific Linear B-Cell Epitopes To Differentiate between Infected and Vaccinated Cattle; publication; Aug. 2003; 7 pages, pp. 8633-8639; vol. 77, No. 16; Journal of Virology; American Society for Microbiology.
A.N.K. Jacob et al.; Nucleotide sequence of the 3' terminal region of belladonna mottle virus-Iowa (renamed Physalis mottle virus) RNA and an analysis of the relationships of tymoviral coat proteins; publication; 1992; 11 pages, p. 367-377; vol. 123; Archives of Virology; Springer-Verlag 1992; Austria.

(Continued)

*Primary Examiner*—Stacy B Chen
(74) *Attorney, Agent, or Firm*—Reinhart Boerner Van Deuren, P.C.

(57) ABSTRACT

The present disclosure relates to chimeric tymovirus-like particles (TVLPs) comprising a fusion protein that further comprises of a first protein that is a truncated tymovirus coat protein and a second protein. These chimeric TVLPs are useful as antigens. The present disclosure provides a highly efficient means for differentiating Foot and Mouth Disease Virus (FMDV) infected animals from vaccinated animals. The present disclosure further provides a process for the production of chimeric TVLPs and a diagnostic kit for the determination of specific antibodies of FMDV to differentiate FMDV infected from vaccinated animals. The present disclosure also provides the use of the chimeric TVLPs for diagnostic purposes.

7 Claims, 5 Drawing Sheets

OTHER PUBLICATIONS

Figure 1:
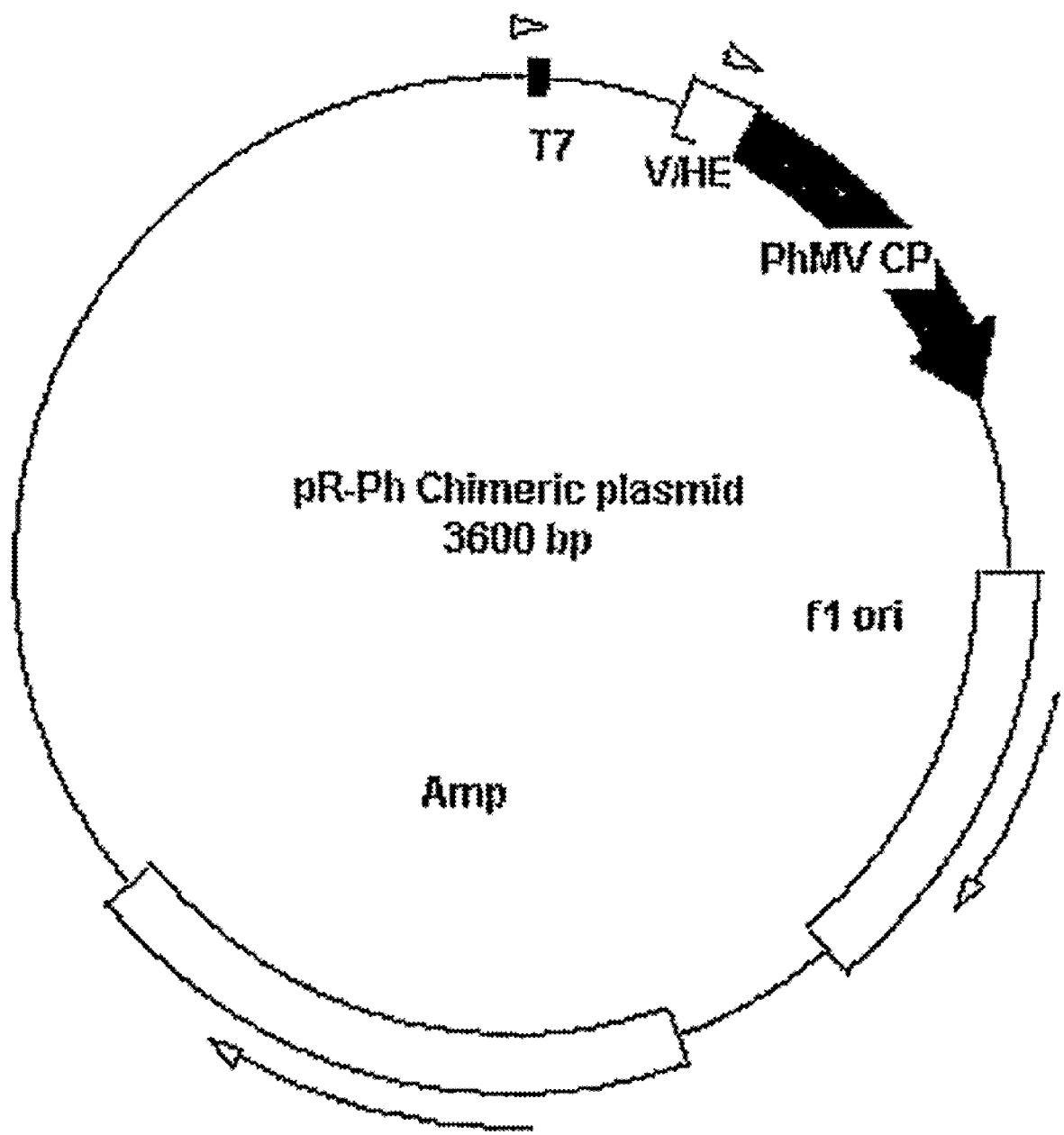

Jae Ku Oem et al.; Development of synthetic peptide ELISA based on nonstructural protein 2C of foot and mouth disease virus; publication; 2005; 9 pages, pp. 317-325; vol. 6(4); Journal of Veterinary Science.

U.K. Laemmli; Cleavage of Structural Proteins during the Assembly of the Head of Bacteriophage T4; publication; Aug. 15, 1970; 6 pages, pp. 680-685; vol. 227; Nature Publishing Group.

D.K.J. Mackay et al.; Differentiating infection from vaccination in foot-and-mouth disease using a panel of recombinant, non-structural proteins in ELISA; publication; 1998; 14 pages, pp. 446-459; vol. 16, No. 5; Vaccine; Elsevier Science Ltd.; Great Britain.

Mira Sastri et al.; Assembly of Physalis Mottle Virus Capsid Protein in *Escherichia coli* and the Role of Amino and Carboxy Termini in the Formation of the Icosahedral Particles; publication; 1997; 12 pages, pp. 541-552; vol. 272; J, Mol. Biol.; Academic Press Limited.

Blanca Robiolo et al.; Analysis of the immune response to FMDV structural and non-structural proteins in cattle in Argentina by the combined use of liquid phase and 3ABC-ELISA tests; publication; 2006; 12 pages, pp. 997-1008; vol. 24; Vaccine; Elsevier.

F. Shen et al.; Differentiation of convalescent animals from those vaccinated against foot-and-mouth disease by a peptide ELISA; publication; 1999; 11 pages, pp. 3039-3049; vol. 17; Vaccine; Elsevier.

K.J. Sorensen et al.; Differentiation of infection from vaccination in foot-and-mouth disease by the detection of antibodies to the non-structural proteins 3D, 3AB and 3ABC in ELISA using antigens expressed in baculovirus; publication; 1998; 16 pages, pp. 1461-1476; vol. 143; Archives of Virology; Springer-Verlag; Austria.

K.J. Sorensen et al.; Differentiation of foot-and-mouth disease virus infected animals from vaccinated animals using a blocking ELISA based on baculovirus expressed FMDV 3ABC antigen and a 3ABC monoclonal antibody; publication; 2005; 10 pages, pp. 805-814; vol. 150; Archives of Virology; Austria.

Tao Sun et al.; Localization of infection-related epitopes on the non-structural protein 3ABC of foot-and-mouth disease virus and the application of tandem epitopes; publication; 2004; 8 pages, pp. 79-86; vol. 119; Journal of Virological Methods; Science Direct; Elsevier.

Kitching, R.P.; Future research on foot and mouth disease; publication; 2002; 5 pages, pp. 885-889; Rev. sci. tech. Off. Int. Epiz., 2002, 21 (3).

Niedbalski, W.; Detection of foot-and-mouth disease virus infection in vaccinated cattle; publication; 2005; 5 pages, pp. 283-287; vol. 8, No. 4; Polish Journal of Veterinary Sciences.

Sambrook, I. et al.; Molecular cloning in A Laboratory Manua; pages from a book; 1989; 2nd edit.; Cold Spring Harbor, NY; Protocol 1, Preparation of Plasmid DNA by Alkaline Lysis with SDS: Minipreparation; 3 pages, pp. 1.32-1.34.

* cited by examiner

CHIMERIC TYMOVIRUS-LIKE PARTICLES AND PROCESS THEREOF

CROSS-REFERENCE TO RELATED PATENT APPLICATIONS

This patent application is a continuation of co-pending PCT Application No. PCT/IN2006/000342, filed Sep. 11, 2006, which claims the benefit of Indian Patent Application No. 486/CHE/2006, filed Mar. 17, 2006, the entire teachings and disclosure of which are incorporated herein by reference thereto.

FIELD OF INVENTION

This disclosure relates to chimeric tymovirus-like particles (TVLPs) comprising fusion protein consisting of structural protein of Physalis mottle tymovirus (PhMV) and peptides/epitopes of virus or hormone. These chimeric TVLPs are used as antigens. The present disclosure provides a highly efficient means for differentiating FMDV infected animals from vaccinated animals. The present disclosure also relates to the use of said chimeric tymovirus-like particles for diagnostic purposes.

BACKGROUND OF THE INVENTION

Foot and mouth disease (FMD) is one of the most contagious, acute viral diseases of cloven-footed animals such as cattle, sheep, goats and pigs (Brown, 2003). FMD is caused by foot and mouth disease virus (FMDV), belongs to *Aphthovirus* genus in the family Picornaviridae. Airborne transmission is the common method of spread while the disease also spreads through fomites. FMD is controlled by stamping out method in non-endemic countries and by vaccination in endemic countries (Grubman and Baxt, 2004).

Current conventional vaccine is an inactivated whole-virus preparation (Doel, 2003). The difficulties involved in differentiating vaccinated from infected animals have kept many countries away from adopting the strategy of FMD vaccination as primary method of control. It is necessary to differentiate vaccinated animals from infected animals using a reliable and accurate diagnostic test if non-endemic countries can consider vaccination as a method of control during an outbreak.

Antibodies principally to the structural proteins of FMDV are induced in vaccinated animals, whereas infected animals produce antibodies to both structural and non-structural proteins (NSP) (Sun et al., 2004). Therefore, assays demonstrating antibodies against non-structural proteins have potential to differentiate infected animals from those that have been vaccinated. The antibodies against polyprotein 3ABC have been proved to be the most reliable marker of FMDV infection. ELISA utilizing recombinant proteins produced either in *E. coli* or baculovirus are used to distinguish the vaccinated animals from infected animals (De Diego et al., 1997; Mackay et al., 1998; Sorensen et al., 1998; Shen et al., 1999; Kitching., 2002; Chung et al., 2002; Clavijo et al., 2004a, 2004b; Sorensen et al., 2005; Robiolo et al., 2005; Niedbalski, 2005). Specificity of 2C and 3D polypeptides were also tested, but were found to be less sensitive when compared to 3ABC polypeptide (Sorensen et al., 1998; Jae Ku Oem et al., 2005).

Shen et al. (1999) used synthetic peptides containing B-cell epitopes of FMDV non-structural proteins and reported that the immunoreactivity to 2C peptides was primarily to those from N-terminal region of the protein. Further recently, the overlapping synthetic peptides were used to identify FMDV infection-specific linear B-cell epitopes to differentiate infected from vaccinated cattle (Hohlich et al., 2003; Sun et al., 2004). Indirect ELISA based on a long (57 amino acid) synthetic peptide was used by Shen et al., (1999), but synthesis of long peptides is difficult. Therefore, short peptide of 20 amino acids was suggested by Hohlich et al. (2003) which has inherent problems due to their weak binding to solid surface. This is the main factor that affects the efficiency and sensitivity of solid phase immunoassay using synthetic peptide as an antigen.

Except as otherwise indicated, the disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

SUMMARY OF THE INVENTION

The present disclosure relates to chimeric tymovirus-like particles (TVLPs) comprising of a fusion protein consisting of a first protein which is a truncated structural tymovirus coat protein and a second protein. Second protein may be peptides/epitopes of virus or hormone. These chimeric TVLPs are useful as antigens. The present disclosure further provides a highly efficient means for differentiating Foot and Mouth Disease virus (FMDV) infected animals from vaccinated animals. The present disclosure also provides a process for the production of chimeric tymovirus-like particles and a diagnostic kit for the determination of specific antibodies of FMDV to differentiate FMDV infected from vaccinated animals. The present disclosure also relates to the use of said chimeric tymovirus-like particles for diagnostic purposes.

One aspect of the disclosure is to provide A chimeric tymovirus-like particle comprising a fusion protein, wherein the fusion protein comprises a first protein that is a truncated tymovirus coat protein and a second protein, wherein the second protein is selected from a group consisting of Foot and Mouth Disease Virus (FMDV) protein, Canine parvoviral (CPV) coat protein, Canine Distemper Virus P35 polypeptide (CDV P35), Gonadotropin releasing hormone (GnRH) and a combination thereof.

Another aspect of the present disclosure is to provide the chimeric TVLPs comprising a fusion protein consisting of a first protein which is a truncated Physalis Mottle tymovirus (PhMV) coat protein and a the second protein is selected from a group consisting of Foot and Mouth Disease Virus (FMDV) protein, Cannine parvoviral (CPV) coat protein, Canine Distemper Virus P35 polypeptide (CDV P35), Gonadotropin releasing hormone (GnRH) protein and a combination thereof.

In yet another aspect, the present disclosure provides a recombinant polynucleotide sequence encoding the fusion protein wherein the polynucleotide is selected from a group consisting of SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, a fragment or a variant thereof.

In yet another aspect, the present disclosure provides a process for the production of chimeric tymovirus-like particle comprising:

a. producing a recombinant polynucleotide sequence coding for a fusion protein, b. constructing a recombinant vector comprising a regulatory sequence and the recombinant polynucleotide sequence of step (a),
c. transforming a host cell with the recombinant vector of step (b) to produce a recombinant host cell,
d. growing the recombinant host cell of step (c) to produce chimeric tymovirus-like particles,
e. purifying the chimeric tymovirus-like particles of step (d).

Still yet another aspect of the present disclosure is to provide a test kit for the determination of specific antibodies against FMDV non-structural proteins, the kit comprising:
a. chimeric tymovirus-like particles comprising fusion protein selected from a group consisting of SEQ ID NO: 3, SEQ ID NO: 5, SEQ ID NO: 7, SEQ ID NO: 9 and SEQ ID NO: 11 encoded by the recombinant polynucleotide sequences as shown in SEQ ID NO: 4, SEQ ID NO: 6, SEQ ID NO: 8, SEQ ID NO: 10 and SEQ ID NO: 12, and;
b. reagents for detection of antibodies.

Still yet another aspect of the present disclosure is to provide a method for detection of specific antibodies against FMDV in a sample, said method comprising contacting the sample with chimeric tymovirus-like particles comprising fusion protein selected from a group consisting of SEQ ID NO: 3, SEQ ID NO: 5, SEQ ID NO: 7, SEQ ID NO: 9 and SEQ ID NO: 11 encoded by the recombinant polynucleotide sequences as shown in SEQ ID NO: 4, SEQ ID NO: 6, SEQ ID NO: 8, SEQ ID NO: 10 and SEQ ID NO: 12, and detecting the formation of the complex between said antibodies and said particles.

BRIEF DESCRIPTION OF ACCOMPANYING DRAWINGS

Figure 2:
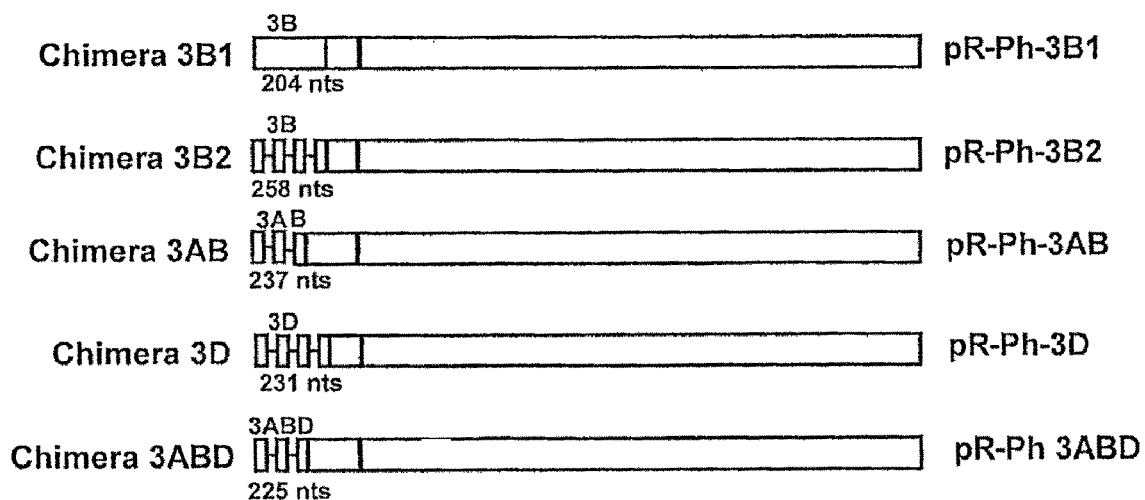
Figure 3:
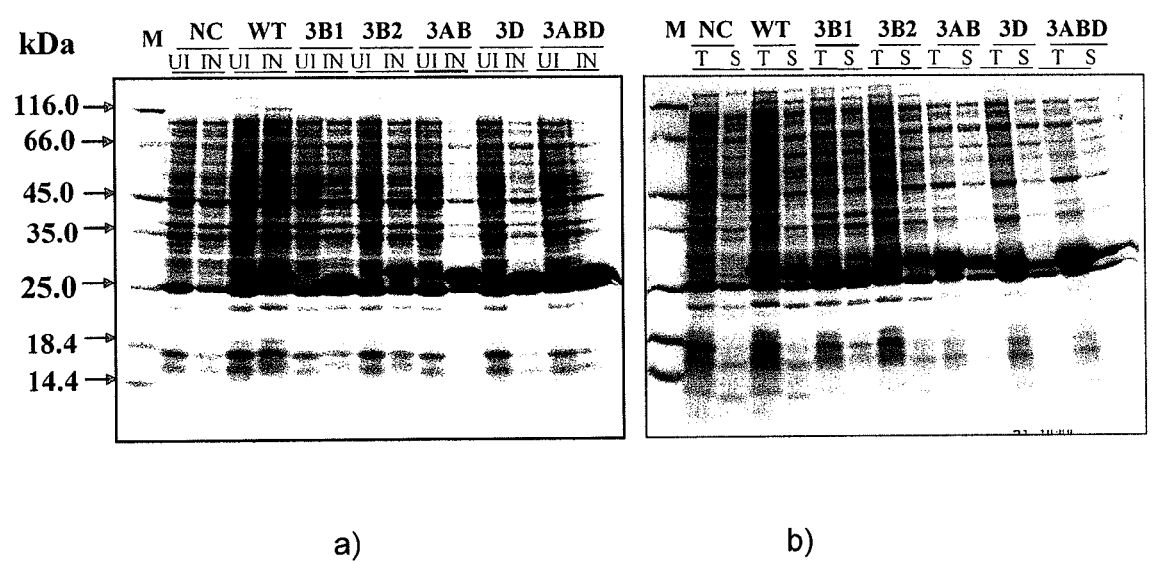
Figure 4:
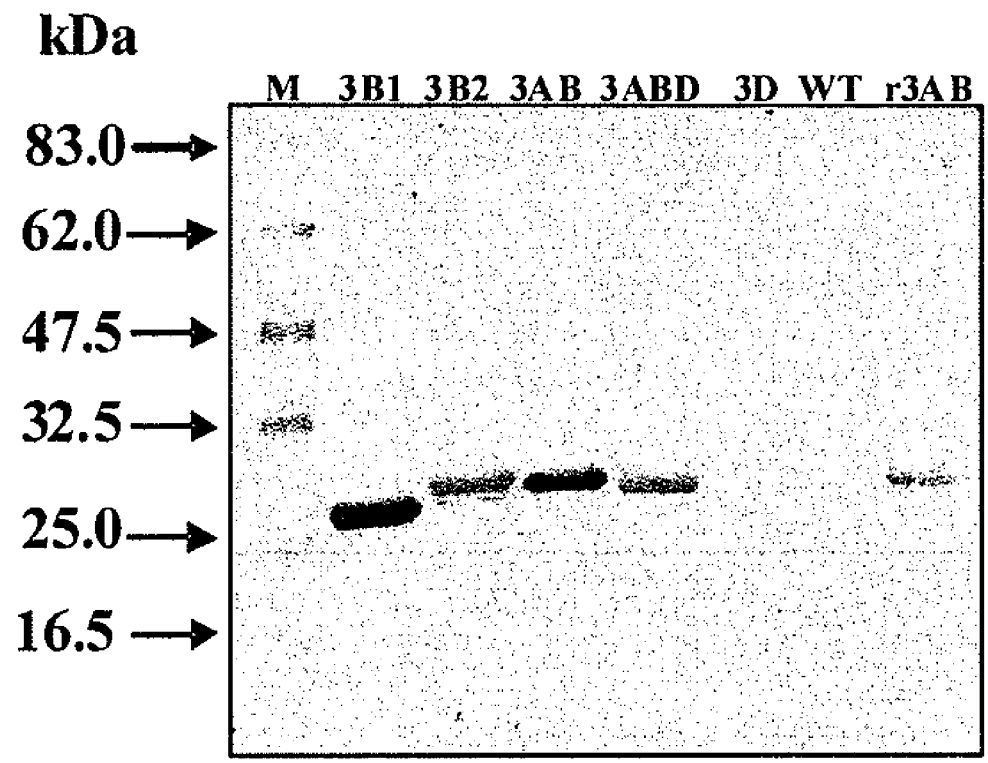
Figure 5:
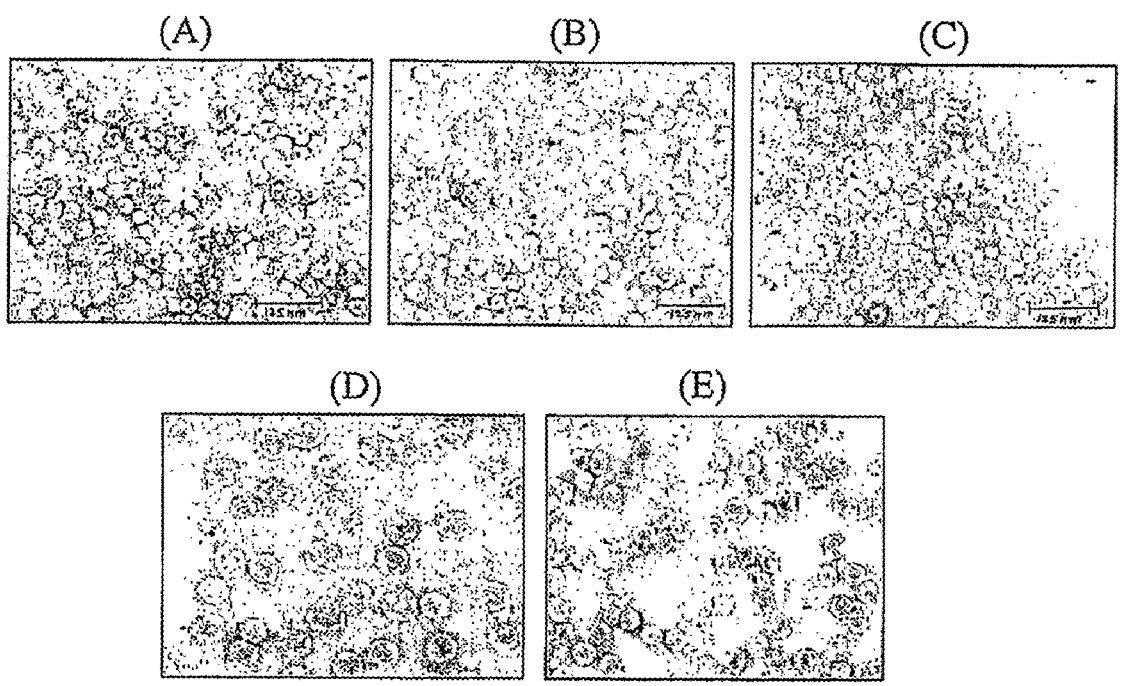

FIG. 1 is a Map of recombinant plasmid pR-Ph SET-A.
FIG. 2 is a Schematic representation of FMDV non-structural protein (NSP) chimeric constructs of 3B1, 3B2, 3AB, 3D and 3ABD.
FIG. 3 is a SDS-PAGE analysis of
a. Uninduced (UI) and induced (IN) fractions of pRSET-A (negative control; NC), pR-Ph-CP (wild-type; WT), pR-Ph-3B1, pR-Ph-3B2, pR-Ph-3AB, pR-Ph-3D and pR-Ph-3ABD expressed in E. coli,
b. Induced total (T) and soluble (S) fractions of pRSET-A (NC), pR-Ph-CP (WT), pR-Ph-3B1, pR-Ph-3B2, pR-Ph-3AB, pR-Ph-3D and pR-Ph-3ABD expressed in E. coli,
c. Lane M shows the standard molecular weight markers (MBI Fermentas).
FIG. 4 is a Western blot analysis of chimeric tymovirus-like particles Ph-3B1, Ph-3B2, Ph-3AB, Ph-3D, Ph-3ABD. Ph-CP is PhMV wild-type empty capsid used as negative control. r3AB is recombinant 3AB expressed in E. coli as positive control. Gel was electro-blotted and then probed with rabbit 3AB polyclonal antiserum (1:2000) raised against r3AB and HRP labeled anti-rabbit goat antiserum (1:1000) was used as secondary antibody. Lane M represents the prestained protein molecular weight marker (NEB).
FIG. 5 is a Electron micrographs of chimeric tymovirus-like particles (80× resolution)
A) Ph-3B1
B) Ph-3B2
C) Ph-3AB
D) Ph-3D
E) Ph-3ABD

DETAILED DESCRIPTION OF THE INVENTION

The present disclosure relates to chimeric tymovirus-like particles (TVLPs) comprising of fusion protein consisting of structural protein of Physalis Mottle Virus (PhMV) and B-cell infection related epitopes of 3B, 3AB, 3D and 3ABD non structural proteins of Foot and Mouth Disease Virus (FMDV) or any other animal/human virus or hormone. These chimeric TVLPs are used as antigens for the differentiation of FMDV infected animals from vaccinated animals. The present disclosure also teaches the use of said chimeric tymovirus-like particles for diagnostic purposes.

The present disclosure further relates to a process of production of chimeric tymovirus-like particles and development of a sensitive and accurate assay to differentiate FMDV infected animals from vaccinated animals by detecting the presence of antibodies against 3B, 3AB, 3D and 3ABD nonstructural proteins in the tested sera samples.

Plant viral VLPs as epitope presentation systems are advantageous when compared to other systems-(1) plant viral VLPs are more economical to make than traditional expression systems (2) the absence of risk of contamination with animal pathogens (3) the possibility of very large scale production (4) the potential for producing sensitive specific diagnostic kits for different purposes (5) risk of transmission of disease is minimal or nil (6) there is no biosafety concerns either in laboratory or in the field (Johnson, 1997; Porta and Lomonossoff, 1998). The majority of the cases, plant, animal infectious viruses were manipulated and also used as VLP based epitope presentation systems for the use as vaccine candidates. VLPs were used for the detection of rubella virus and procine enteric virus (Keros and Enders, 1997; Guo et al., 2001). To the best of our knowledge no diagnostic kit on VLP based epitope presentation system has been developed. This is the first report where Tymoviral VLPs (TVLPs) are able to present FMDV 3B, 3AB, 3ABD and 3D non-structural epitopes (proteins/peptides) on the surface of TVLPs and these chimeric tymovirus-like particles are useful in the differentiation of FMDV infected animals from uninfected or vaccinated animals successfully by ELISA.

In one embodiment the present disclosure provides a chimeric tymovirus-like particle comprising a fusion protein, wherein the fusion protein comprises a first protein that is a truncated tymovirus coat protein and a second protein, wherein the second protein is selected from a group consisting of Foot and Mouth Disease Virus (FMDV) protein, Canine parvoviral (CPV) coat protein, Canine Distemper Virus P35 polypeptide (CDV P35), Gonadotropin releasing hormone (GnRH) and a combination thereof.

In another embodiment the disclosure provides a chimeric tymovirus-like particle comprising fusion protein consisting of first protein which is truncated tymovirus coat protein and second protein, wherein the tymovirus is selected from a group consisting of Physalis Mottle Virus, Belladonna Mottle Virus, Turnip Yellow Mosaic Virus, Cacao Yellow Mosaic Virus, Clitoria Yellow Vein Virus, Desmodium Yellow Mottle Virus, Egg Plant Mosaic Virus and Passion Fruit Yellow Mosaic Virus.

In another embodiment the disclosure provides a chimeric tymovirus-like particle comprising first protein which is a truncated tymovirus coat protein, wherein the truncated tymovirus coat protein is truncated Physalis mottle virus (PhMV) coat protein.

In another embodiment the present disclosure provides a chimeric tymovirus-like particle comprising a fusion protein consisting of first protein and second protein.

In another embodiment the disclosure provides a chimeric tymovirus-like particle comprising first protein which is a truncated tymovirus coat protein, wherein the truncated tymovirus coat protein comprising at least 149 contiguous amino acids of the amino acid sequence as shown in SEQ ID NO: 1.

In another embodiment the disclosure provides a chimeric tymovirus-like particle comprising first protein which is a truncated tymovirus coat protein, wherein the truncated tymovirus coat protein is encoded by a polynucleotide sequence as shown in SEQ ID NO: 2, a fragment or a variant thereof.

In another embodiment the disclosure provides a chimeric tymovirus-like particle comprising first protein which is a truncated tymovirus coat protein, wherein the polynucleotide sequence comprising at least 447 contiguous nucleotides of the polynucleotide sequence as shown in SEQ ID NO: 2.

In yet another embodiment the present disclosure provides a truncated tymovirus coat protein comprising at least 149 contiguous amino acids of the amino acid sequence as shown in SEQ ID NO: 1 encoded by a polynucleotide sequence comprising at least 447 contiguous nucleotides is as shown in SEQ ID NO: 2, a fragment or a variant thereof.

Still yet another embodiment of the present disclosure, the fusion protein is having polypeptide sequence selected from a group consisting of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33.

Further embodiment of the present disclosure provides the fusion protein selected from a group consisting of SEQ ID NO: 3, SEQ ID NO: 5, SEQ ID NO: 7, SEQ ID NO: 9, SEQ ID NO: 11 encoded by the recombinant polynucleotide sequence as shown in SEQ ID NO: 4, SEQ ID NO: 6, SEQ ID NO: 8, SEQ ID NO: 10 and SEQ ID NO: 12.

In one embodiment the present disclosure provides a chimeric tymovirus-like particle comprising a fusion protein, wherein the fusion protein is encoded by a recombinant polynucleotide sequence.

Still another embodiment of the present disclosure discloses a chimeric tymovirus-like particle comprising a fusion protein, wherein the fusion protein comprises a first protein that is a truncated Physalis Mottle Virus (PhMV) coat protein and a second protein, wherein the second protein is selected from a group consisting of Foot and Mouth Disease Virus (FMDV) protein, Cannine parvoviral (CPV) coat protein, Canine Distemper Virus P35 polypeptide (CDV P35), Gonadotropin releasing hormone (GnRH) and a combination thereof.

Still another embodiment of the present disclosure discloses a recombinant polynucleotide sequence encoding the fusion protein, wherein the recombinant polynucleotide sequence is selected from a group consisting of SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30 SEQ ID NO: 32, SEQ ID NO: 34, a fragment or a variant thereof.

Still another embodiment of the present disclosure provides a recombinant vector comprising an expression cassette, the expression cassette further comprises a regulatory sequence and a recombinant polynucleotide sequence selected from a group consisting of SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30 SEQ ID NO: 32, SEQ ID NO: 34, a fragment or a variant thereof, wherein the regulatory sequence is selected from a group consisting of T7, SP6 and T3.

In another embodiment the disclosure provides a recombinant vector which is selected from a group consisting of pR-Ph-CP, pR-Ph-3B1, pR-Ph-3B2, pR-Ph-3AB, pR-Ph-3D, pR-Ph-3ABD, pR-Ph-VP1-C1, pR-Ph-VP1-C2, pR-Ph-VP1-C3, pR-Ph-IC-C1, pR-Ph-IC-C2, pR-Ph-IC-C3, pR-Ph-CPV1, pR-Ph-CPV2, pR-Ph-CPV3, pR-Ph-CPV4 and pR-Ph-CPV5.

In one embodiment the present disclosure provides a host cell comprising the recombinant vector. The host cell is selected from a group consisting of E. coli, yeast and baculovirus.

In yet another embodiment the present disclosure provides E. coli strain selected from a group consisting of JM101, DH5α, BL21, HB101, BL21 (DE3) pLys S, XL-1 Blue and Rossetta.

In one embodiment the present disclosure relates to a process for production of chimeric tymovirus-like particle, the process comprises:
(a) producing a recombinant polynucleotide sequence,
(b) constructing a recombinant vector comprising a regulatory sequence and the recombinant polynucleotide sequence of step (a),
(c) transforming a host cell with the recombinant vector of step (b) to produce a recombinant host cell,
(d) growing the recombinant host cell of step (c) to produce chimeric tymovirus-like particles,
(e) purifying the chimeric tymovirus-like particles of step (d).

In another embodiment the present disclosure relates to a process for production of chimeric tymovirus-like particle comprising the step of constructing a recombinant vector comprising a regulatory sequence and the recombinant polynucleotide sequence disclosed in the invention, wherein the regulatory sequence is selected from a group consisting of T7, SP6 and T3.

In another embodiment the present disclosure relates to a process for production of chimeric tymovirus-like particle, wherein the recombinant polynucleotide sequence is selected from a group consisting of SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 and SEQ ID NO: 34.

In another embodiment the present disclosure relates to a process for production of chimeric tymovirus-like particle, wherein the recombinant vector is selected from a group consisting of pR-Ph-CP, pR-Ph-3B, pR-Ph-3B2, pR-Ph-3AB, pR-Ph-3D, pR-Ph-3ABD, pR-Ph-VP1-C1, pR-Ph-VP1-C2, pR-Ph-VP1-C3, pR-Ph-IC-C1, pR-Ph-IC-C2, pR-Ph-IC-C3, pR-Ph-CPV1, pR-Ph-CPV2, pR-Ph-CPV3, pR-Ph-CPV4 and pR-Ph-CPV5.

In yet another embodiment the present disclosure provides a test kit for determination of specific antibodies against FMDV, the kit comprising:
(a) chimeric tymovirus-like particles comprising fusion protein selected from a group consisting of SEQ ID NO: 3, SEQ ID NO: 5, SEQ ID NO: 7, SEQ ID NO: 9 and SEQ ID NO: 11 encoded by the recombinant polynucleotide sequences as shown in SEQ ID NO: 4, SEQ ID NO: 6, SEQ ID NO: 8, SEQ ID NO: 10 and SEQ ID NO: 12, and,
(b) reagents for detection of antibodies.

In yet another embodiment the present disclosure provides a method for detection of specific antibodies against FMDV in a sample, said method comprising contacting the sample with chimeric tymovirus-like particles comprising fusion protein selected from a group consisting of SEQ ID NO: 3, SEQ ID NO: 5, SEQ ID NO: 7, SEQ ID NO: 9 and SEQ ID NO: 11 encoded by the recombinant polynucleotide sequences as shown in SEQ ID NO: 4, SEQ ID NO: 6, SEQ ID NO: 8, SEQ ID NO: 10 and SEQ ID NO: 12, and detecting the formation of the complex between said antibodies and said particles.

PhMV, is a small spherical plant virus, a member of the tymovirus genus of positive-stranded RNA viruses was first isolated by Moline & Fries (1974) in Iowa, USA. The positive-sense RNA genome is encapsidated in a protein shell consisting of 180 identical copies of CP (20,000 kDa) arranged with T=3 icosahedral symmetry in which there are three distinct bonding patterns. Depending on the bonding interactions the chemically identical subunits are called A, B and C. Five A type subunits form pentamers at the 12, 5-fold icosahedral axes (a total of 60 subunits) and the B and C type subunits form hexamers at the 20 icosahedral 3-fold axes (120 subunits). A comparison of coat protein sequence of PhMV with other tymoviruses revealed that it had 52% identity with belladonna mottle virus (E) and 33% identity with turnip yellow mosaic virus (TYMV), showing that PhMV (previously named as belladonna mottle virus I) was a distinct tymovirus (Mira et al., 1997; 1999).

PhMV offers the following advantages:
(1) The genome is small (2) It is easy to manipulate (3) Purification is simple and quicker than the regeneration of stably transformed plants. Coat protein of PhMV expresses extremely well as empty capsids in *E. coli* resulting in (1) Yields as high as 100-150 mg per liter of culture, (2) Batch to batch variations are nil as each and every time confirmation of the assembled capsids will be maintained in a similar way for the integrity of the capsids, (3) Recombinant Ph-CP is stable over a wide range of pH from 4.2 to 9.0 and stable upto 4 M urea, (4) Purification of empty capsids is easy (5)

Mechanism of assembly of empty capsids is well studied. (6) Host range is very narrow (Mira et al., 1997, 1999).

Chimeric virus-like particle Ph-3AB was tested using ELISA for differentiation of infected animals from uninfected or vaccinated animals. The convalescent sera samples collected from infected animals (by virus isolation) were tested by ELISA and all the sera reacted well with the chimeric TVLP Ph-3AB. Uninfected samples collected from naive animals did not react with chimeric TVLP Ph-3AB. The recombinant antigen generated is useful in differentiating infected animals from uninfected animals either vaccinated or non-infected animals. Other chimeric TVLPs were also tested using ELISA.

The ready, inexpensive and safe availability of the antigen and the suitability of the simple indirect ELISA method is useful for:
1) rapid detection of carrier animals in the presence or absence of vaccination,
2) monitoring the progress of FMDV eradication programs and
3) epidemiological surveys in regions which practice vaccination.

This approach is different from genetic transformation of plants where it needs integration of the gene of interest into the plant genome and use of plant virus-based vectors as platforms for delivery purposes. Considering the biosafety measures, VLPs are safe as there is no risk of transmission of infectious organism. This approach does not need the development of infectious cDNA clones for the manipulation of the genomes.

The DNA sequence coding for the Physalis Mottle Virus (PhMV) was identified from the GenBank having EMBL accession number S97776 (Jocob et al., 1992). The truncated PhMV coat protein consists of 159-175 amino acid residues of wild type PhMV coat protein. The coat protein was synthetically produced using the methods well known in the art. B-cell infection related epitopes of FMDV non-structural protein 3ABD were identified based on prior information (Hohlich et al., 2003, Sun et al., 2004). Nucleotide sequence (SEQ ID NO: 12) encoding the protein 3ABD (SEQ ID NO: 11) was synthesized in the laboratory using methods well known in the art. The DNA sequence encoding this protein is as shown in SEQ ID NO: 11. Detailed procedure is provided in Example 1.

Gene encoding different epitopes of FMDV such as 3B (SEQ ID NO: 4 and 6), 3AB (SEQ ID NO: 8), 3D (SEQ ID NO: 10) and 3ABD (SEQ ID NO: 12); antigenic epitopes of FMDV VP1 (SEQ ID NO: 14, SEQ ID NO: 16 and SEQ ID NO: 18), Gonadotropin releasing hormone (GnRH) SEQ ID NO: 20, GnRH in combination with CDV P35 (SEQ ID NO: 22 and SEQ ID NO: 24) and antigenic peptides of Canine Parvovirus (CPV) (SEQ ID NO: 26, SEQ ID NO: 28, SEQ ID NO: 30, SEQ ID NO: 32 and SEQ ID NO: 34) were cloned in plasmid vectors such as pRSET-A, pPCR, pQE, pET series and pGEX for cloning and expression. All the constructs were made synthetically with NdeI site at the 5' end followed by different combinations of these epitopes as tandem repeats with Glycine-Glycine-Serine (GGS) linker in between along with a part of wild-type PhMV CP sequence in frame up to Kpn I site at the 3' end. Detailed procedure is described in Example 2.

Recombinant vectors namely pR-Ph-CP, pR-Ph-3B1, pR-Ph-3B2, pR-Ph-3AB, pR-Ph-3D and pR-Ph-3ABD were transformed in host cells selected from a group consisting of *E. coli*, Yeast and Baculovirus. For details see Example 3.

The host cells containing the recombinant vectors were grown in suitable media for overexpression of the fusion protein (see Example 4, 10 and 11) and the fusion protein was purified (see Example 5). The methods used for overexpression and purification of the fusion protein are well known in the art.

The Immunological characterization of chimeric tymovirus-like particles (TVLPs) was carried out by various methods well known in the art. The detailed procedure is provided in Example 6. ELISA has been performed to check the display of animal viral proteins or hormone on the surface of PhMV TVLP. Further, Western blotting was carried out to check the specificity of the chimeric tymovirus-like particles (TVLPs). Characterization studies of chimeric tymovirus-like particles (TVLPs) were carried out using transmission electron microscopy (see Example 7). Indirect ELISA was carried out to detect FMDV infected animals from vaccinated animals using chimeric TVLPs. Different PhMV chimeric antigens viz. Ph-3B1, Ph-3B2, Ph-3AB, Ph-3D and Ph-3ABD were screened in an indirect ELISA format against different sera. Wild type PhMV antigen and the recombinant *E. coli* cell expressing recombinant antigen Ph-3AB was also included as negative and positive antigen controls, respectively. The detailed procedure is provided in Example 8.

FMDV is a member of the Picornavirus family. The viral genome consists of positive sense 8.5 kb ssRNA, which is encapsidated in an icosahedral capsid composed of 60 copies each of four structural proteins designated VP1, VP2, VP3 and VP4 which are secondary cleavage products of P1 polyprotein. Among them, VP1 is the immunodominant region which contains 3 important antigenic sites. The precise location of B and T cell epitopes of the capsid protein VP1 has been established flanking amino acid residues 21-40, 135-160 and 200-213. Expression analysis of FMDV-VP1 structural protein epitopes was carried out. Details are given in Example 9.

Immunocastration is an alternative to surgical castration method. Gonadotropin releasing hormone (GnRH), a very small protein of 10 amino acids produced from hypothalamic neurons. It is a poor antigen and needs to be conjugated to carrier proteins. Anti GnRH vaccines are used to decrease the accumulation of skatole and androsterones in the fatty tissue of pigs, which leads to boar taint in pork meat. Canine distemper virus P35 (CDV P35) is a T cell epitope of fusion protein and shown to be very effective in eliciting anti GnRH antibodies in male dogs when conjugated with GnRH. Induction of high titer antibody specific for GnRH correlated with the regression of testes. Anti GnRH vaccines have potential application in cancer therapies including breast and prostate cancer. Expression analysis of Gonadotropin releasing hormone was done. The detailed procedure is given in the Example 10.

Canine Parvovirus (CPV) belongs to the feline parvovirus subgroup of the genus Parvorirus within the family Parvoviridae. It causes an important disease in dogs and is endemic throughout the world. CPV infection in dogs is characterized by enteritis of variable severity and is often associated with a relative lymphopoenia. Acute myocarditis occurs in puppies up to 16 weeks of age and causes 50-80% mortality. Current vaccines are based on live attenuated viruses. A limitation of the vaccine is that in puppies, maternally derived antibodies hinder the development of a protective immunity. This could also hold good for recombinant VP2 capsids when they are used as immunogens. For such cases, synthetic or subunit vaccines might present a preferable alternative. Epitope-mapping studies of the capsid protein indicated the presence of a number of antigenic sites which were recognized by neutralizing sera. Expression of CPV-VP2 epitopes in E. coli was analyzed. For detailed procedure refer Example 11.

The present disclosure is important that it can be applied to present the other economically important animal/human pathogen epitopes for diagnostic or vaccine or therapeutic purpose. Although the foregoing invention has been described in detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are put forth so as to provide those of ordinary skill in the art with a complete disclosure and the description of how to make and use the present invention, and are not intended to limit the scope of what the inventors regard as their invention nor are they intended to represent that the experiments below are all and only experiments performed.

Example 1

Synthesis of Physalis Mottle Virus Coat Protein Gene

The DNA sequence coding for the Physalis Mottle Virus (PhMV) coat protein (CP) was extracted from the GenBank. (EMBL Accession number: S97776). This gene was made synthetically with Xho I and Hind III sites at 5' and 3' ends, respectively and with a stop codon at the end of the reading frame, without the start codon at the beginning of the gene. A Kpn I site was introduced as silent mutation at 44 and 45 amino acids of the coat protein for the purpose of swapping heterologous sequences.

Synthesis of FMDV Non-Structural Peptide Genes

The DNA coding for epitopes as tandem repeats of 3B1, 3B2, 3AB, 3D and 3ABD with linkers consisting of 144, 198, 147, 153 and 165 nucleotides, respectively with Nde I at the 5' end and a part of PhMV sequence until Kpn I site at the 3' end of the genes were synthetically produced.

The cloning procedure and strategy was same for all the chimeras like FMDV non-structural protein (NSP) constructs, FMDV-VP1 constructs, GnRH constructs and CPV constructs. All the polynucleotide sequences containing tandem repeats, linkers and a part of PhMV sequence till Kpn I site were produced synthetically with Nde I and Kpn I sites at 5' and 3' ends and cloned into pPCR Script cloning vector.

Example 2

Construction of Recombinant Vectors

Cloning of the Coat Protein (CP) Gene in Vector pRSET-A

Wild type PhMV CP (SEQ ID NO: 2) was made synthetically with Xho I and Hind III sites on 5' and 3' ends, respectively which was cloned in plasmid vector pPCR Script. This wild type CP insert of 564 bp was released from pPCR Script vector by digesting with Xho I and Hind III and was cloned at Xho I and Hind III sites of the pRSET-A expression vector. For this, plasmid vectors pPCR Script containing wild type PhMV CP and pRSET-A vector were restricted with Xho I and Hind III enzymes. Xho I and Hind III fragment of wild type PhMV-CP and restricted pRSET-A vector were eluted by gel extraction method and ligation was carried out. The insert DNA in this recombinant vector was confirmed by DNA sequencing methods known in the art. In this case, the reading frame starts at the ATG with in the NdeI site of the vector, so the wild-type coat protein (SEQ ID NO: 1) has 39 amino acids extra from the vector backbone and with a stop codon before the Hind III site. The size of the recombinant CP vector was 3435 bp in length. The recombinant vector was designated as pR-Ph-CP.

Cloning of Modified Viral/Hormone Gene

DNA fragment coding for virus/hormone protein was swapped in pR-Ph-CP at Nde I and Kpn I restriction sites. The DNA fragments coding for virus protein may be from 3B1, 3B2, 3AB, 3D and 3ABD epitopes of FMDV and DNA fragments coding for hormonal protein may be from GnRH gene.

The synthetic DNA sequence coding for 3ABD was inserted at sites created by the restriction enzymes Nde I and Kpn I to produce a recombinant vector. For this, plasmid vectors pPCR Script containing 3ABD gene and pR-Ph-CP vector were restricted with Nde I and Kpn I enzymes. Nde I and Kpn I fragment of 3ABD gene and restricted pR-Ph-CP vector were eluted by gel extraction method and ligation was carried out. The recombinant vector is named as pR-Ph-3ABD. The insert DNA in this recombinant vector was confirmed by DNA sequencing methods known in the art. Similarly DNA fragments coding for 3B1, 3B2, 3AB and 3D epitopes of FMDV, VP1 epitopes of FMDV, DNA fragments coding for hormonal protein from GnRH gene in combination with CDV P35 epitope and CPV VP2 epitopes were cloned in pR-Ph-CP at Nde I and Kpn I sites. The recombinant vectors were named as pR-Ph-CP, pR-Ph-3B1, pR-Ph-3B2, pR-Ph-3AB, pR-Ph-3D, pR-Ph-3ABD, pR-Ph-VP1-C1, pR-Ph-VP1-C2, pR-Ph-VP1-C3, pR-Ph-IC-C1, pR-Ph-IC-C2, pR-Ph-IC-C3, pR-Ph-CPV1, pR-Ph-CPV2, pR-Ph-CPV3, pR-Ph-CPV4 and pR-Ph-CPV5. The ligation mix was transformed into E. coli strain DH5α. The plasmid was isolated from E. coli strain DH5α containing recombinant vector and authenticity of the recombinants was confirmed by sequencing. Positive clones were transformed in BL-21 (DE3) pLys S strain for expression of the fusion protein.

All the virus/hormone gene inserts are in the range of 200-300 nucleotides and were made synthetically with Nde I and Kpn I sites and swapped at the Nde I and Kpn I digested vector of pR-Ph-CP, such that that portion of the wild type CP will be substituted with heterologous sequence and rest of the wild type protein will be there in all the constructs without disturbing the reading frame (FIG. 1). FIG. 2 represents the FMDV non-structural protein (NSP) chimeric constructs viz. 3B1, 3B2, 3AB, 3D and 3ABD, where B-cell infection related epitopes of 3A, 3B, 3D and 3ABD in tandem with linkers were substituted at the N-terminal part of the PhMV wild-type coat protein.

Example 3

Transformation of *E. coli*

Competent cells of *E. coli* were prepared using calcium chloride as described by Sambrook et al (1989). For transformation either DH5-α or BL 21 (DE3) pLys S competent cells were mixed with the DNA on ice, followed by a brief heat shock at 42° C. for 45 seconds. Cells were incubated with rich medium and allowed to grow for 30-60 min at 37° C. prior to plating. Constructs containing recombinant genes under the control of the T7 polymerase transformed into DH5-α for cloning purpose, but need to be transformed into a different bacterial strain, BL21 (DE3) pLys S for expression of the recombinant protein. The recombinant vector pR-Ph-3ABD was transformed into *E. coli* DH5a strain to produce recombinant *E. coli* cells. These recombinant *E. coli* cells are named as r-Ph-3ABD. Similarly other recombinant vectors pR-Ph-3B1, pR-Ph-3B2, pR-Ph-3AB and pR-Ph-3D were transformed into *E. coli* DH5-α strain to produce recombinant *E. coli* cells namely r-Ph-3B1, r-Ph-3B2, r-Ph-3AB and r-Ph-3D respectively.

Example 4

Overexpression and Purification of Chimeric Tymovirus-Like Particles in *E. coli*

The recombinant *E. coli* r-Ph-3ABD was grown in suitable media overnight at 37° C. The cells were harvested by centrifugation. Plasmids were isolated from recombinant cells containing different plasmids such as pR-Ph-3ABD, pR-Ph-3B1, pR-Ph-3B2, pR-Ph-3AB and pR-Ph-3D using methods well known in the art. Plasmid DNA isolation was carried out by the alkaline lysis method as described (Sambrook et al., 1989). For expression study, pRSET-A vector (negative control), the wild-type and recombinant vectors were transformed into BL21 (DE3) pLysS strain of *E. coli*. The transformation resulted in recombinant *E. coli* cells having the recombinant plasmids.

The recombinant *E. coli* cells were grown in the growth medium for expression of the fusion protein using the methods well known in the art. The fusion proteins were named as Ph-3B1, Ph-3B2, Ph-3AB, Ph-3D and Ph-ABD. Fusion proteins were isolated using methods well known in the art. SDS-PAGE was carried using discontinuous buffer system described by Laemmli (Laemmli, 1970) using slab gel electrophoresis apparatus. Throughout this study 1 mm thick 15% polyacrylamide (30:0.8, acrylamide to bisacrylamide ratio) gel containing 0.1% SDS was used for electrophoretic separation of proteins. The protein samples were mixed with an equal volume of 2× sample buffer (100 mM Tris-HCl pH 6.8 containing 2% SDS, 0.02% bromophenol blue, 10% β-ME and 20% glycerol) and heated at 95° C. for 5 min and were loaded into the wells of precise polyacrylamide gel. Electrophoresis was performed at a constant voltage at 100 V using 0.025 M Tris and 0.2 M glycine buffer pH 8.8 containing 0.1% SDS. After the electrophoresis, the gel was either stained with commassie brilliant blue or processed for western blotting. Single colony of recombinant *E. coli* strain was inoculated in Luria-Bertani (LB) medium containing 100 μg/ml ampicillin and 33 μg/ml chloramphenicol. 5 ml of LB media was inoculated with 1% overnight culture, grown for three hours at 37° C. and induced with 0.5 mM isopropyl-1-thio-β-D-galactopyranoside (IPTG). Two hours later, the cells were harvested and resuspended in 500 μl of distilled water. An aliquot of the cells were taken for the protein analysis. An equal volume of 2×SDS-PAGE loading buffer was added to 20 μl of resuspended cells and used for the analysis of total cell proteins by using SDS-PAGE analysis (FIG. 3). The remaining cells were sonicated for ten minutes using a cell sonicator and centrifuged at 27,000 g for ten minutes, the soluble fraction was collected and the insoluble fraction was suspended in 500 μl of distilled water. The total and soluble fractions were analyzed by SDS/(w/v) 15% PAGE (Laemmli, 1970). The methods for analysis of proteins were carried out as known in the art.

Example 5

Purification of Chimeric Tymovirus-Like Particles

For large-scale purification of the wild-type and chimeric TVLPs, the procedure known in the art was carried out (Mira et al., 1997, 1998). The cells were suspended in 50 mM sodium citrate buffer (pH 5.5), sonicated and the soluble fraction was subjected to 10% (w/v) polyethylene glycol (6000) precipitation followed by a high-speed ultra-centrifugation (140,000 g, 3 hr). The precipitate was resuspended in 50 mM sodium citrate buffer and layered onto a 10-40% sucrose gradient. The light scattering zone was collected, diluted and subjected to ultra-centrifugation (140,000 g, 3 hr). The pellets obtained were resuspended in 50 mM sodium citrate buffer (pH 5.5). The purity of the chimeric TVLPs was checked by SDS/15% PAGE (Laemmli, 1970). SDS-PAGE analysis of uninduced, induced fractions of pRSET-A, wild-type, 3B1, 3B2, 3AB, 3D, 3ABD and induced total and soluble fractions of pRSET-A, wild-type, 3B1, 3B2, 3AB, 3D, 3ABD expressed in *E. coli*, was carried out (FIG. 3). Lane M shows the standard molecular weight markers. All the recombinant plasmids expressed well along with wild-type PhMV coat protein. Protein expression was induced and induced protein fractions were compared with uninduced fractions (FIG. 3A) and there is no expression seen in the fractions where vector (pRSET-A; negative control) alone was expressed. Soluble protein fractions of vector alone, wild-type CP and chimeric plasmids were compared with total protein fractions and found that considerable amount of protein is present in the soluble fraction (FIG. 3B).

Example 6

Immunological Characterization of Chimeric Tymovirus-Like Particles (TVLPS)

The wild type and chimeric TVLPs were separated on SDS15% acrylamide gel and transferred onto nitrocellulose membranes. The western blot analysis was carried out using rabbit 3AB antiserum (1:2000) raised against r-3AB (recombinant 3AB expressed in *E. coli*) and HRP labeled anti-rabbit goat antiserum (1:1000) was used as secondary antibody. The blot was developed using Diamino benzidine (DAB) in the presence of hydrogen peroxide in 0.05 M sodium citrate buffer (pH 4.8) containing trace amounts of cobalt chloride. Ph-3B1, Ph-3B2, Ph-3AB, Ph-ABD were reacted well with 3AB antiserum along with positive control r3AB. Wild-type PhMV CP and Ph-3D did not reacted with the 3AB antiserum (FIG. 4)

Example 7

Electron Microscopy

The wild-type CP and chimeric TVLPs such as Ph-3B1, Ph-3B2, Ph-3AB, Ph-3ABD and Ph-3D and (0.5 mg/ml) were applied onto carbon coated grids and stained with Uranyl acetate (2%; w/v). These grids were visualized by a high resolution electron microscope (Hitachi H 7500) at a magnification of 80×. Chimeric TVLPs are looking exactly like wild-type PhMV empty capsids (Mira et al., 1997) under electron microscope (FIG. 5)

Example 8

Indirect ELISA to Differentiate FMDV Infected from Vaccinated Animals Using Chimeric TVLPs ELISA plates were sensitized by over night incubation at 4° C. with an optimum dilution of purified chimeric 3AB TVLP antigen (40 ng/50 µl/well) or wild type purified PhMV TVLP antigen (40 ng/50 µl/well) in carbonate-bicarbonate coating buffer. One well was left as no antigen control for each sample. The reagents used for ELISA are well known in the art. In suitable tubes all test and control sera were blocked overnight at 4° C. by preparing pre-dilutions at a dilution of 1:5 in blocked ELISA diluent (10 µl serum in 40 µl blocking buffer). Alternatively, the sera were prepared and incubated at 37° C. for 2 hours on a plate shaker. The next day the plates were washed with wash buffer (Phosphate buffered saline with Tween 20 (0.05%) and flick dried. 50 µl of each pre diluted blocked serum was transferred to the marked wells of the ELISA plates. The plates were incubated at 37° C. on a plate shaker for 1 hour. The plates were washed with wash buffer, flick dried. 50 µl of appropriate dilution of HRP conjugated anti-species IgG in blocked ELISA diluent was added to the plates and incubated at 37° C. on a plate shaker for 1 hour. Then the plates were washed with a wash buffer, flick dried. 50 µl of ice cold Chromogen/Substrate mix i.e. OPD/$H_2O_2$ at appropriate dilution was added and the plates were incubated for 5 min at room temperature in dark. The reaction was stopped with 1M $H_2SO_4$. The plates were read at 492 nm using a ELISA plate reader. The antigen blank wells and wells containing the wild type Physalis Mottle virus VLP antigen must show an OD of <0.100. Around 100 numbers of negative sera were tested and the cut-off value was derived from the calculated mean and the standard deviation (SD). Once the cut-off value was derived 40 known positive samples (FMDV carrier status confirmed by virus isolation in primary organ cell culture) were tested using the chimeric TVLP 3AB. 80 samples with known history of FMD were tested. Also 80 samples of unknown history were also tested. ELISA was carried out using other chimeric proteins. The assay clearly indicated that ELISA is highly specific based on the negative and positive samples.

Differentiation of Vaccinated and Infected Animals (DIVA) Using Chimeric TVLPs

Reactivity of FMDV-NSP Chimeric TVLPs Towards Experimental Serum Samples:

The different Chimeric TVLPs viz. Ph-3B1, Ph-3B2, Ph-3AB, Ph-3ABD and Ph-3D were screened in an indirect ELISA format against different sera. Wild type PhMV VLP and an *E. coli* expressed recombinant 3AB (*E. coli* r-3AB) was also included as negative and positive antigen controls. The bovine convalescent sera (BCS) were known positive bovine sera for FMDV-NSP antibodies; one serum each obtained from affected and unaffected animal of bovine origin was also included in the testing. Normal bovine serum was used as a negative control. The reactivity of the antigen was also compared with other sera that included an immune mouse and immune rabbit sera raised against *E. coli* r-3AB antigen while unimmunized mouse and rabbit serum acted as controls. The other controls used were a growth medium control and Phosphate buffered saline.

| Experimental Serum | Ph-3B1 | | Ph-3B2 | | Ph-3AB | | Ph-3ABD | | Ph-3D | | Ph-CP (Wild Type) | | *E. coli* r-3AB | |
|---|---|---|---|---|---|---|---|---|---|---|---|---|---|---|
| Type O BCS | 0.258 | 0.275 | 0.164 | 0.154 | 0.230 | 0.237 | 0.279 | 0.261 | 0.109 | 0.125 | 0.046 | 0.045 | 0.479 | 0.448 |
| Type A BCS | 0.186 | 0.217 | 0.093 | 0.115 | 0.102 | 0.120 | 0.168 | 0.179 | 0.082 | 0.084 | 0.042 | 0.044 | 0.336 | 0.271 |
| Type C BCS | 0.298 | 0.297 | 0.182 | 0.172 | 0.229 | 0.236 | 0.291 | 0.280 | 0.253 | 0.285 | 0.046 | 0.046 | 0.486 | 0.493 |
| Type ASIA1 BCS | 0.279 | 0.262 | 0.144 | 0.146 | 0.220 | 0.225 | 0.234 | 0.248 | 0.122 | 0.119 | 0.045 | 0.046 | 0.246 | 0.415 |
| Known Positive BS | 0.294 | 0.312 | 0.196 | 0.196 | 0.279 | 0.256 | 0.290 | 0.294 | 0.120 | 0.120 | 0.045 | 0.044 | 0.498 | 0.499 |
| Known Negative BS | 0.043 | 0.042 | 0.047 | 0.046 | 0.044 | 0.042 | 0.051 | 0.044 | 0.042 | 0.046 | 0.040 | 0.043 | 0.174 | 0.168 |
| Normal BS | 0.047 | 0.050 | 0.046 | 0.053 | 0.047 | 0.049 | 0.047 | 0.048 | 0.045 | 0.043 | 0.043 | 0.043 | 0.059 | 0.056 |
| Growth Medium Control | 0.056 | 0.058 | 0.054 | 0.068 | 0.060 | 0.056 | 0.058 | 0.049 | 0.048 | 0.044 | 0.041 | 0.041 | 0.088 | 0.096 |
| r-3AB IMS | 0.298 | 0.323 | 0.144 | 0.138 | 0.183 | 0.188 | 0.194 | 0.178 | 0.201 | 0.205 | 0.049 | 0.054 | 0.460 | 0.462 |
| Anti 3AB MAb 3C7 | 0.120 | 0.125 | 0.111 | 0.112 | 0.108 | 0.105 | 0.104 | 0.100 | 0.095 | 0.095 | 0.043 | 0.043 | 0.393 | 0.441 |
| Normal MS | 0.049 | 0.047 | 0.050 | 0.060 | 0.056 | 0.046 | 0.043 | 0.041 | 0.042 | 0.041 | 0.042 | 0.044 | 0.055 | 0.051 |
| r-3AB IRS | 0.307 | 0.337 | 0.113 | 0.127 | 0.147 | 0.126 | 0.116 | 0.107 | 0.135 | 0.134 | 0.059 | 0.060 | 0.097 | 0.100 |
| r-MVA 3AB IRS | 0.424 | 0.415 | 0.147 | 0.148 | 0.176 | 0.165 | 0.151 | 0.130 | 0.155 | 0.155 | 0.052 | 0.055 | 0.083 | 0.091 |
| Normal RS | 0.076 | 0.054 | 0.050 | 0.050 | 0.064 | 0.053 | 0.057 | 0.042 | 0.043 | 0.042 | 0.054 | 0.073 | 0.060 | 0.056 |
| PBS Control | 0.065 | 0.062 | 0.071 | 0.063 | 0.056 | 0.058 | 0.056 | 0.050 | 0.052 | 0.049 | 0.049 | 0.068 | 0.052 | 0.065 |

Note:
BCS—Bovine Convalescent Serum; BS—Bovine Serum; IMS—Immune Mouse Serum; MAb—Monoclonal Antibody; MS—Mouse Serum; IRS—Immune Rabbit Serum; RS—Rabbit Serum; PBS—Phosphate Buffered Saline The PhMV Chimeric TVLPs reacted in different sensitivities with different sera. Ph-3B2, Ph-3AB and Ph-3ABD reacted well with all the sera. Ph-3B2 did not react with type A BCS, r-3AB IMS, r-3AB IRS and r-MVA 3AB IRS (MVA: Modified Vaccinia Ankara). Ph-3D did not react with any of the positive sera except type C BCS and r-3AB IMS. Consistent reaction was noticed with Ph-3AB and Ph-3ABD antigens with BCS indicated that the FMDV NSP epitopes got displayed well on the surface of the PhMV TVLPs. None of the chimeric TVLPs reacted with the monoclonal antibody Anti 3AB MAb 3C7. Wild type PhMV TVLP did not show any reaction to the different sera while E. coli r-3AB antigen reacted well with almost all the sera except r-MVA 3AB IRS.

Standardization of Assay:

The assay was standardized using known positive samples and known negative samples (samples provided by IAH, Pirbright Lab, UK). Sera collected from animals that were positive by virus isolation test were considered as known positive samples (n=40) while sera collected from animals that were negative by virus isolation test were considered as known negative samples. Indirect ELISA was performed with 50 ng of Ph-3AB antigen. 36 out of 40 known positive samples were positive with Ph-3AB while all the 100 known negative samples were negative with Ph-3AB.

Estimation of Cut-Off Value:

The cut off was estimated as Mean+Thrice Standard Deviation–0.150 for Ph-3AB and Ph-3ABD ELISAs. Ph-3D ELISA was discontinued because it was not sensitive. Fifty four goat and thirty six sheep sera that were negative by virus isolation were tested and the cut-off was fixed at 0.230.

Testing of Sera:

The assay was performed using known positive samples and known negative samples (samples were derived from various cattle challenge experiments).

| Result | Ph-3AB2 | Ph-3ABD | Ph-3D | Cedi Test |
|---|---|---|---|---|
| Positives | 74 | 67 | 52 | 77 |
| Negatives | 3 | 10 | 25 | 0 |

74 out of 77 known positive samples were positive with Ph-3AB antigen while only 67 were positive with Ph-3ABD antigen. Ph-3D antigen could detect only 52 out of 77 positive samples. All 90 known negative samples were declared negative in all the three tests. The test was compared against Ceditest for the positive samples and the results showed that Ph-3AB was more specific than the other two chimeric antigens.

i. Comparison of PhMV-Chimeras—Known Positive Serum

| | | Ph-3ABD | | Ph-3D | |
|---|---|---|---|---|---|
| | | Positive | Negative | Positive | Negative |
| Ph-3AB | Positive | 66 | 8 | 51 | 23 |
| | Negative | 1 | 2 | 1 | 2 |

| | | Ph-3AD | |
|---|---|---|---|
| | | Positive | Negative |
| Ph-3ABD | Positive | 51 | 16 |
| | Negative | 1 | 9 |

Out of the 77 samples tested by three chimeric antigens, 66 were positive by both Ph-3AB and Ph-3ABD while 2 were negative by both the tests. However, 8 samples that were declared positive by Ph-3AB were declared negative by Ph-3ABD and only 1 which was positive by Ph-3ABD was declared negative by Ph-3AB. Similarly out of the 77 samples tested by the three Chimeric antigens, 52 were positive by both Ph-3AB and Ph-3D while 2 were negative by both the tests. However, 23 samples that were declared positive by Ph-3AB were declared negative Ph-3D and only 1 which was positive by Ph-3ABD was declared negative by Ph-3AB. This shows that Ph-3AB was more sensitive than the other two chimeric antigens.

Screening of Random Sera Samples Collected from Field Using Ph-3AB and Ph-3ABD ELISA:

89 sera samples collected from cattle from different places randomly were tested with Ph-3AB and Ph-3ABD ELISA and the results were as follows:

| Result | Ph-3AB | Ph-3ABD | Ph-3D | Ceditest |
|---|---|---|---|---|
| Positives | 23 | 13 | 1 | 25 |
| Negatives | 66 | 76 | 88 | 64 |

23 samples were declared positive by Ph-3AB, 13 by Ph-3ABD and only one by Ph-3D when compared with 25 that were declared positive by Ceditest.

i) Comparison of PhMV-Chimeras—Field Serum

| | | Ph-3AB | | Ph-3ABD | | Ph-3D | |
|---|---|---|---|---|---|---|---|
| | | Positive | Negative | Positive | Negative | Positive | Negative |
| CEDI TEST | Positive | 23 | 2 | 10 | 15 | 1 | 24 |
| | Negative | 0 | 64 | 3 | 61 | 0 | 64 |

Out of the 25 samples declared positive by Ceditest there was agreement in 23 samples in Ph-3AB, 10 samples in Ph-3ABD and only 1 with Ph-3D. Out of the 64 samples that were declared negative by Ceditest complete agreement was noticed in Ph-3AB and Ph-3D while only 61 samples agreed with the results in Ph-3ABD. This shows that the Ph-3ABD test may not be as specific as the other tests. Two samples that were positive with Ceditest were declared negative in PhMV-3AB while 15 and 24 samples were declared negative by Ph-3ABD and Ph-3D respectively indicating that the specificity of these two tests was low when compared to Ceditest or Ph-3AB.

Development of internal controls for Ph-3AB ELISA: 40 known positive sera and 40 known negative sera were tested against Ph-3AB to develop internal standards. Results: The results were similar with Ph-3AB and Ph-3ABD ELISA and by Ceditest.

Ph-3AB Based ELISA for Cattle Buffalo Sheep and Goats Sheep Samples (n=61):

The Ph-3AB ELISA was put use to screen sheep samples collected randomly from an organized farm in Tamil Nadu. The comparative results with Ceditest are given below.

|  | CEDITEST | |
|---|---|---|
| ORGANIZED FARM | Positive | Negative |
| Ph-3AB Positive | 24 | 4 |
| Negative | 6 | 24 |

The results indicated that 24 samples were declared positive by both the tests while 24 were declared negative by both the tests. However, the two tests disagreed with regard to 10 samples.

Swine Samples (n=39):

The Ph-3AB ELISA was put use to screen 39 swine samples collected from different places. The comparison of results against Ceditest is give below.

|  | Ceditest | |
|---|---|---|
| Swine samples | Positive | Negative |
| Ph-3AB Positive | 13 | 1 |
| Negative | 1 | 24 |

The results indicated that 13 samples were declared positive by both the tests while 24 were declared negative by both the tests. However, the two tests disagreed with regard to 2 samples.

ii. Total Number of Sera Tested by Ph-3AB ELISA and Comparison with Ceditest

| SPECIES | PH-3AB ELISA | CEDITEST | |
|---|---|---|---|
|  |  | Positive | Negative |
| Cattle | Positive | 237 | 0 |
|  | Negative | 5 | 204 |
| Sheep & Goats | Positive | 24 | 4 |
|  | Negative | 6 | 114 |
| Swine | Positive | 13 | 1 |
|  | Negative | 1 | 24 |

Ph-3AB based ELISA is very specific (100%) based on the negative samples tested. Ph-3AB based ELISA is as sensitive as Ceditest. When compared with the Ceditest the sensitivity of Ph-3AB ELISA was 95.80%, while the sensitivity of the Ceditest when compared with Ph-3AB ELISA was 98.21. Few samples that were declared NSP antibodies negative by Ceditest were positive by Ph-3AB based ELISA and vice versa.

Example 9

Expression Analysis of FMDV-VP1 Structural Protein Epitopes

DNA fragments coding for FMDV-VP1 neutralizing epitopes were cloned in pR-Ph-CP in Nde I and Kpn I restriction sites to produce recombinant vectors pR-Ph-VP1-C1, pR-Ph-VP1-C2 and pR-Ph-VP 1-C3. The insert DNA in this recombinant vector was confirmed by DNA sequencing methods known in the art. These recombinant vectors were transformed into E. coli strain DH5 α. The recombinant E. coli cells containing said recombinant vectors were designated as r-Ph-VP1-C1, r-Ph-VP1-C2 and r-Ph-VP1-C3. The plasmid was isolated from E. coli strain DH5α containing recombinant vector and transformed in E. coli BL21 (DE3) pLys S strain for expression of the fusion proteins. The chimeric TVLPs were designated as Ph-VP1-C1, Ph-VP1-C2 and Ph-VP1-C3 having amino acid sequence as shown in SEQ ID NO: 13, and 17. The detailed procedure is provided in Example 3.

The recombinant E. coli cells were grown in the growth medium for production of the chimeric tymovirus-like particles as described in Example 4. Chimeric TVLPs purification was carried out using the procedure as described in Example 5.

Example 10

Expression Analysis of Gonadotropin Releasing Hormone

DNA fragment coding for GnRH protein was cloned in pR-Ph-CP in Nde I and Kpn I restriction sites to produce recombinant vectors pR-Ph-IC-C1 DNA fragment of GnRH in combination with CDV P35 DNA sequence in tandem repeats was also cloned in pR-Ph-CP in Nde I and Kpn I restriction sites to produce recombinant vectors pR-Ph-IC-C2 and pR-Ph-IC-C3.

The insert DNA in this recombinant vector was confirmed by DNA sequencing methods known in the art. These recombinant vectors were transformed into E. coli strain DH5-α. The recombinant E. coli cells containing said recombinant vectors were designated as r-Ph-IC-C1, r-Ph-IC-C2 and r-Ph-IC-C3. The plasmid was isolated from E. coli strain DH5-α containing recombinant vector and transformed in E. coli (DE3) pLys S strain for expression of the fusion proteins. The chimeric TVLPs were designated as Ph-IC-C1, Ph-IC-C2 and Ph-IC-C3 having amino acid sequence as shown in SEQ ID NO: 19, 21 and 23. The detailed procedure is provided in Example 3.

The recombinant E. coli cells were grown in the growth medium for production of the chimeric tymovirus-like particles as described in Example 4. Chimeric TVLPs purification was carried out using the procedure as described in Example 5.

Example 11

Expression of CPV-VP2 VLPs

DNA fragment coding for antigenic peptide sites of Canine Parvovirus (CPV) was cloned in pR-Ph-CP in Nde I and Kpn I restriction sites to produce recombinant vectors pR-Ph-CPV. DNA fragment of antigenic peptide sites of CPV in tandem repeats was cloned in pR-Ph-CP in Nde I and Kpn I restriction sites to produce recombinant vectors pR-Ph-CPV1, pR-Ph-CPV2, pR-Ph-CPV3, pR-Ph-CPV4 and pR-Ph-CPV5.

The insert DNA in this recombinant vector was confirmed by DNA sequencing methods known in the art. These recombinant vectors were transformed into E. coli strain DH5-α. The recombinant E. coli cells containing said recombinant vectors were designated as r-Ph-CPV1, r-Ph-CPV2, r-Ph-CPV3, r-Ph-CPV4 and r-Ph-CPV5. The plasmid was isolated from recombinant E. coli (DH5-α) cells containing recombinant vector and transformed in E. coli (DE3) pLys S strain for expression of the fusion proteins. The chimeric TVLPs were designated as Ph-CPV1, Ph-CPV2, Ph-CPV3, Ph-CPV4 and Ph-CPV5 having amino acid sequence as shown in SEQ ID NO: 25, 27, 29, 31 and 33. The detailed procedure of E. coli transformation is provided in Example 3.

The recombinant E. coli cells were grown in the growth medium for production of the chimeric tymovirus-like particles as described in Example 4. Chimeric TVLPs purification was carried out using the procedure as described in Example 5.

REFERENCES

1. Brown F, 2003. The history of research in foot-and-mouth disease. Virus Research. 91: 3-7.
2. Chung W, K J Sorensen, P Liao, P Yang and M Jong. 2002. Differentiation of foot-and-mouth diease virus-infected from vaccinated pigs by enzyme-linked immunosorbent assay using nonstructural protein 3AB as the antigen and application to an eradication program. J of Clinical Microbiology 40(8):2843-2848.
3. Clavijo A, P Wright and P Kitching. 2004a. Developments in diagnostic techniques for differentiating infection from vaccination in foot and mouth disease. The Veterinary Journal 167: 9-22.
4. Clavijo A, Zhou E, Hole K, Galic B, Kitching P 2004b. Development and use of a biotinylated 3ABC recombinant protein in a solid-phase competitive ELISA for the detection of antibodies against foot-and-mouth disease virus. J of Virological Methods 120: 217-227.
5. De Diego et al., 1997. The non-structural polyprotein 3ABC of foot and mouth dieease virus as a diagnostic antigen in ELISA to differentiate infected from vaccinated cattle. Arch Virol 142: 2021-2033.
6. Doel T R. 2003. FMD vaccines. Virus Research. 91: 81-89.
7. Grangeot-Keros L and G Enders 1997. Evaluation of a new enzyme immunoassay based on recombinant rubella virus-like particles for detection of immunoglobulin M antibodies to Rubella virus. J of Clinical Microbiology. 35(2): 398-401.
8. Grubman M J and Baxt Barry. 2004. Foot-and-mouth disease. Clinical Microbiology Reviews. 465-493.
9. Guo M, Y Qian, K Chang and L J. Saif. 2001. Expression and self-assembly in baculovirus of porcine enteric calcivirus capsids into virus-like particles and their use in an enzyme-linked immunoassay for antibody detection in swine. Journal of Clinical Microbiology 39(4) 1487-1493.
10. Hohlich et al., 2003. Identification of foot and mouth disease virus-specific linear B-cell epitopes to differentiate between infected and vaccinated cattle. J Virol, 77: 8633-8639.
11. Jocob et al., 1992. Nuceotide sequence of the 3' terminal region of belladonna mottle virus-Iowa (renamed physalis mottle virus) RNA and an analysis of the relationships of a tymoviral coat proteins. Archives of Virology. 123: 367-377.
12. Jae Ku Oem et al., 2005. Development of synthetic peptide ELISA based on nonstructural protein 2C of foot and mouth disease virus J Vet Sci 6: 317-325.
13. Johnson et al., 1997. Presentation of heterologous peptides on plant viruses: Genetics, structure and function. Annu. Rev. Phytopathol., 35: 67-86.
14. Kitching R P. 2002. Identification of foot and mouth disease virus carrier and subclinically infected animals and differentiation from vaccinated animals. Rev Sci Tech. 21:531-538.
15. Laemmli, U K. 1970. Cleavage of structural proteins during the assembly of the head of the bacteriophage T4. Nature. 227: 680-685.
16. Mackay et al., 1998. Differentiating infection from vaccination in foot-and-mount disease using a panel of recombinant non-structural proteins in ELISA. Vaccine 16: 446-459.
17. Mira S, Ramesh K, Gopinath K, Ranjith Kumar C T, Jagath J R and H S Savithri. 1997. Assembly of physalis mottle virus capsid protein in *Escherichia coli* and the role of amino and carboxy termini in the formation of the icosahedral particles. J Mol. Biol., 272: 541-552.
18. Mira S. Srihari Reddy D, Sri Krishna S, Murthy M R N and H S Savithri. 1999. Identification of a discrete intermediate in the assembly/disassembly of physalis mottle tymovirus through mutational analysis. J Mol. Biol., 289:905-918.
19. Moline H E and Fries R E. 1974. A strain of belladonna mottle virus isolated from *Physalis heterophylla* in Iowa. Phytopathology. 64: 44-48.
20. Niedbalski W. 2005. Detection of foot-and mouth disease virus infection in vaccinated cattle. Polish Journal of Veterinary Sciences. 8: 283-287.
21. Porta and Lomonossoff. 1998. Scope for using plant viruses to present epitopes from animal pathogens. Rev Med. Virol., 8: 25-41.
22. Robiolo et al., 2005. Analysis of the immune response to FMDV structural and non-structural proteins in cattle in Argentina by the combined use of liquid phase and 3ABC-ELISA tests. Vaccine (Online).
23. Sambrook I, E F Fritisch and T Maniatis. 1989. Molecular cloning in A Laboratory Manua, 2 nd edit. Cold Spring Harbor Laboratory Press, Cold Spring Harbor, N.Y.
24. Shen et al., 1999. Differentiation of convalescent animals from those vaccinated against foot-and-mount disease by a peptide ELISA. Vaccine 17: 3039-3049.
25. Sorensen et al., 1998. Differentiation of infection from vaccination in foot and mouth disease by the detection of antibodies to the non-structural proteins 3D,3AB and 3ABC ELISA using antigens expressed in baculovirus. Arch Virol., 143: 1461-1476.
26. Sorensen et al., 2005. Differentiation of foot and mouth disease virus infected animals from vaccinated animals using a blocking ELISA based on baculovirus expressed FMDV 3ABC antigen and a 3ABC monoclonal antibody. Arch Virol 150: 805-814.
27. Sun et al., 2004. Localization of infection-related epitopes on the non-structural protein 3ABC of foot-and-mouth disease virus and the application of tandem epitopes. Jounral of Virological Methods 119: 79-86

What is claimed is:

1. A chimeric tymovirus-like particle comprising a fusion protein, wherein the fusion protein comprises a first protein of tymovirus *Physalis* mottle virus (PhMV) coat protein and a second protein, wherein the second protein is Foot and Mouth Disease Virus (FMDV) protein, wherein the first protein comprises at least the 149 contiguous amino acids of the C-terminus of the amino acid sequence as shown in SEQ ID NO: 1.

2. The chimeric tymovirus-like particle as claimed in claim 1, wherein the *Physalis* mottle virus (PhMV) tymovirus coat protein is encoded by a polynucleotide sequence as shown in SEQ ID NO: 2.

3. The chimeric *Physalis* mottle virus (PhMV) tymovirus-like particle as claimed in claim 2, wherein the polynucleotide sequence comprises at least 447 contiguous nucleotides.

4. The chimeric tymovirus-like particle as claimed in claim 1, wherein the fusion protein is selected from a group consisting of SEQ ID NO: 3, SEQ ID NO: 5, SEQ ID NO: 7, SEQ ID NO: 9, SEQ ID NO: 11, SEQ ID NO: 13, SEQ ID NO: 15 and SEQ ID NO: 17.

5. The chimeric tymovirus-like particle as claimed in claim 1, wherein the fusion protein is selected from a group consisting of SEQ ID NO: 3, SEQ ID NO: 5, SEQ ID NO: 7, SEQ ID NO: 9 and SEQ ID NO: 11 encoded by the recombinant polynucleotide sequences as shown in SEQ ID NO: 4, SEQ ID NO: 6, SEQ ID NO: 8, SEQ ID NO: 10 and SEQ ID NO: 12.

6. The chimeric tymovirus-like particle as claimed in claim 1, wherein the fusion protein is encoded by a recombinant polynucleotide sequence.

7. The chimeric tymovirus-like particle as claimed in claim 6, wherein the recombinant polynucleotide sequence is selected from a group consisting of SEQ ID NO: 4, SEQ ID NO: 6, SEQ ID NO: 8, SEQ ID NO: 10, SEQ ID NO: 12, SEQ ID NO: 14, SEQ ID NO: 16 and SEQ ID NO: 18.

\* \* \* \* \*

SEQUENCE LISTING

```
<160> NUMBER OF SEQ ID NOS: 34

<210> SEQ ID NO 1
<211> LENGTH: 187
<212> TYPE: PRT
<213> ORGANISM: Physalis Mottle Virus
```

<400> SEQUENCE: 1

```
Asp Ser Ser Glu Val Val Lys Val Lys Gln Ala Ser Ile Pro Ala Pro
1               5                   10                  15
Gly Ser Ile Leu Ser Gln Pro Asn Thr Glu Gln Ser Pro Ala Ile Val
            20                  25                  30
Leu Pro Phe Gln Phe Glu Ala Thr Thr Phe Gly Thr Ala Glu Thr Ala
        35                  40                  45
Ala Gln Val Ser Leu Gln Thr Ala Asp Pro Ile Thr Lys Leu Thr Ala
    50                  55                  60
Pro Tyr Arg His Ala Gln Ile Val Glu Cys Lys Ala Ile Leu Thr Pro
65                  70                  75                  80
Thr Asp Leu Ala Val Ser Asn Pro Leu Thr Val Tyr Leu Ala Trp Val
                85                  90                  95
Pro Ala Asn Ser Pro Ala Thr Pro Thr Gln Ile Leu Arg Val Tyr Gly
            100                 105                 110
Gly Gln Ser Phe Val Leu Gly Gly Ala Ile Ser Ala Ala Lys Thr Ile
        115                 120                 125
Glu Val Pro Leu Asn Leu Asp Ser Val Asn Arg Met Leu Lys Asp Ser
    130                 135                 140
Val Thr Tyr Thr Asp Thr Pro Lys Leu Leu Ala Tyr Ser Arg Ala Pro
145                 150                 155                 160
Thr Asn Pro Ser Lys Ile Pro Thr Ala Ser Ile Gln Ile Ser Gly Arg
                165                 170                 175
Ile Arg Leu Ser Lys Pro Met Leu Ile Ala Asn
            180                 185
```

<210> SEQ ID NO 2
<211> LENGTH: 564
<212> TYPE: DNA
<213> ORGANISM: Artificial
<220> FEATURE:
<223> OTHER INFORMATION: Synthetic

<400> SEQUENCE: 2

```
gactcttcgg aagttgtcaa agtcaagcag gcctccatcc ccgcccctgg ctccattctc      60
tcccagccca acacagaaca atcacctgcc atagttctcc cttttcagtt tgaagccact     120
actttcggta ccgctgaaac cgcagcccaa gtctctctcc agactgccga ccccattacc     180
aaactgaccg cccccctaccg acatgctcag atcgtcgagt gcaaagctat cctcactcca     240
actgatcttg ctgtctccaa tcccctcaca gtctacctag catgggtccc cgccaactcc     300
cctgccactc cgactcaaat actgcgagtc tacggcggtc agtcttttgt tcttggcggc     360
gccatctcag ccgccaaaac cattgaggtc cccctcaatc ttgactctgt caaccgcatg     420
ttgaaagaca gcgtgaccta cactgacacc cccaagctcc ttgcctactc aagagccccc     480
accaacccct cgaaaatccc aaccgctagt attcagatca gcggtcgcat tcggctctcc     540
aagccaatgc tgatagccaa ctaa                                             564
```

<210> SEQ ID NO 3
<211> LENGTH: 210
<212> TYPE: PRT
<213> ORGANISM: Artificial
<220> FEATURE:
<223> OTHER INFORMATION: Synthetic

<400> SEQUENCE: 3

```
Met Gly Pro Tyr Ala Gly Pro Leu Glu Arg Gln Lys Pro Leu Lys Val
1               5                   10                  15

Arg Ala Lys Leu Pro Gln Gln Glu Gly Pro Tyr Ala Gly Pro Met Glu
            20                  25                  30

Arg Gln Lys Pro Leu Lys Val Lys Ala Lys Ala Pro Val Val Lys Glu
        35                  40                  45

Glu Gln Ser Pro Ala Ile Val Leu Pro Phe Gln Phe Glu Ala Thr Thr
    50                  55                  60

Phe Gly Thr Ala Glu Thr Ala Ala Gln Val Ser Leu Gln Thr Ala Asp
65                  70                  75                  80

Pro Ile Thr Lys Leu Thr Ala Pro Tyr Arg His Ala Gln Ile Val Glu
                85                  90                  95

Cys Lys Ala Ile Leu Thr Pro Thr Asp Leu Ala Val Ser Asn Pro Leu
                100                 105                 110

Thr Val Tyr Leu Ala Trp Val Pro Ala Asn Ser Pro Ala Thr Pro Thr
            115                 120                 125

Gln Ile Leu Arg Val Tyr Gly Gln Ser Phe Val Leu Gly Gly Ala
        130                 135                 140

Ile Ser Ala Ala Lys Thr Ile Glu Val Pro Leu Asn Leu Asp Ser Val
145                 150                 155                 160

Asn Arg Met Leu Lys Asp Ser Val Thr Tyr Thr Asp Thr Pro Lys Leu
                165                 170                 175

Leu Ala Tyr Ser Arg Ala Pro Thr Asn Pro Ser Lys Ile Pro Thr Ala
            180                 185                 190

Ser Ile Gln Ile Ser Gly Arg Ile Arg Leu Ser Lys Pro Met Leu Ile
        195                 200                 205

Ala Asn
    210
```

<210> SEQ ID NO 4
<211> LENGTH: 633
<212> TYPE: DNA
<213> ORGANISM: Artificial
<220> FEATURE:
<223> OTHER INFORMATION: Synthetic

<400> SEQUENCE: 4

```
atgggtccgt atgccggtcc gctggaacgt cagaaaccgc tgaaagttcg tgccaaactg       60
ccgcagcagg aaggcccgta cgctggcccg atggagcgcc aaaagccatt aaaggtgaaa      120
gcgaaagcgc cggttgttaa agaagaacag agcccggcga ttgttctgcc gtttcagttt      180
gaagcgacca cctttggtac cgctgaaacc gcagcccaag tctctctcca gactgccgac      240
cccattacca aactgaccgc ccctaccga catgctcaga tcgtcgagtg caaagctatc      300
ctcactccaa ctgatcttgc tgtctccaat cccctcacag tctacctagc atgggtcccc      360
gccaactccc ctgccactcc gactcaaata ctgcgagtct acggcggtca gtcttttgtt      420
cttggcggcg ccatctcagc cgccaaaacc attgaggtcc ccctcaatct tgactctgtc      480
aaccgcatgt tgaaagacag cgtgacctac actgacaccc ccaagctcct tgcctactca      540 agagcccccca ccaaccccctc gaaaatccca accgctagta ttcagatcag cggtcgcatt      600
cggctctcca agccaatgct gatagccaac taa                                    633
```

```
<210> SEQ ID NO 5
<211> LENGTH: 228
<212> TYPE: PRT
<213> ORGANISM: Artificial
<220> FEATURE:
<223> OTHER INFORMATION: Synthetic

<400> SEQUENCE: 5

Met Gly Pro Tyr Ala Gly Pro Leu Glu Arg Gln Lys Pro Leu Lys Gly
1               5                   10                  15

Gly Ser Pro Met Glu Arg Gln Lys Pro Leu Lys Val Lys Ala Lys Ala
            20                  25                  30

Gly Gly Ser Gly Pro Tyr Ala Gly Pro Leu Glu Arg Gln Lys Pro Leu
        35                  40                  45

Lys Gly Gly Ser Pro Met Glu Arg Gln Lys Pro Leu Lys Val Lys Ala
50                  55                  60

Lys Ala Glu Gln Ser Pro Ala Ile Val Leu Pro Phe Gln Phe Glu Ala
65                  70                  75                  80

Thr Thr Phe Gly Thr Ala Glu Thr Ala Ala Gln Val Ser Leu Gln Thr
                85                  90                  95

Ala Asp Pro Ile Thr Lys Leu Thr Ala Pro Tyr Arg His Ala Gln Ile
            100                 105                 110

Val Glu Cys Lys Ala Ile Leu Thr Pro Thr Asp Leu Ala Val Ser Asn
        115                 120                 125

Pro Leu Thr Val Tyr Leu Ala Trp Val Pro Ala Asn Ser Pro Ala Thr
    130                 135                 140

Pro Thr Gln Ile Leu Arg Val Tyr Gly Gly Gln Ser Phe Val Leu Gly
145                 150                 155                 160

Gly Ala Ile Ser Ala Ala Lys Thr Ile Glu Val Pro Leu Asn Leu Asp
                165                 170                 175

Ser Val Asn Arg Met Leu Lys Asp Ser Val Thr Tyr Thr Asp Thr Pro
            180                 185                 190

Lys Leu Leu Ala Tyr Ser Arg Ala Pro Thr Asn Pro Ser Lys Ile Pro
        195                 200                 205

Thr Ala Ser Ile Gln Ile Ser Gly Arg Ile Arg Leu Ser Lys Pro Met
    210                 215                 220

Leu Ile Ala Asn
225

<210> SEQ ID NO 6
<211> LENGTH: 687
<212> TYPE: DNA
<213> ORGANISM: Artificial
<220> FEATURE:
<223> OTHER INFORMATION: Synthetic

<400> SEQUENCE: 6
atgggtccgt atgccggtcc gctggaacgt cagaaaccgc tgaaaggtgg tagcccgatg      60
gagcgccaaa aaccgctgaa ggttaaagcg aaagcgggcg gtagcggccc gtacgctggc     120
ccgttagaac gtcaaaaacc gttaaaaggc ggctctccga tggaacgcca agcgccgtta     180
aaagtgaaag cgaaagccga acagagcccg gcgattgttc tgccgtttca gtttgaagcg     240
accaccttcg gtaccgctga accgcagcc caagtctctc tccagactgc cgaccccatt     300
accaaactga ccgcccccta ccgacatgct cagatcgtcg agtgcaaagc tatcctcact     360
ccaactgatc ttgctgtctc caatcccctc acagtctacc tagcatgggt ccccgccaac     420
tcccctgcca ctccgactca aatactgcga gtctacggcg gtcagtcttt tgttcttggc     480
```

-continued

| | | | | |
|---|---|---|---|---|
| ggcgccatct | cagccgccaa | aaccattgag | gtcccccctca | atcttgactc tgtcaaccgc | 540 |
| atgttgaaag | acagcgtgac | ctacactgac | accccaagc | tccttgccta ctcaagagcc | 600 |
| cccaccaacc | cctcgaaaat | cccaaccgct | agtattcaga | tcagcggtcg cattcggctc | 660 |
| tccaagccaa | tgctgatagc | caactaa | | | 687 |

<210> SEQ ID NO 7
<211> LENGTH: 221
<212> TYPE: PRT
<213> ORGANISM: Artificial
<220> FEATURE:
<223> OTHER INFORMATION: Synthetic

<400> SEQUENCE: 7

Met Asn Glu Tyr Ile Glu Lys Ala Asn Ile Thr Thr Asp Asp Lys Gly
1               5                   10                  15

Gly Ser Gly Pro Tyr Ala Gly Pro Leu Glu Arg Gln Lys Pro Leu Lys
            20                  25                  30

Gly Gly Ser Pro Met Glu Arg Gln Lys Pro Leu Lys Val Lys Ala Lys
        35                  40                  45

Ala Pro Gly Ser Ile Leu Ser Gln Pro Asn Thr Glu Gln Ser Pro Ala
    50                  55                  60

Ile Val Leu Pro Phe Gln Phe Glu Ala Thr Thr Phe Gly Thr Ala Glu
65                  70                  75                  80

Thr Ala Ala Gln Val Ser Leu Gln Thr Ala Asp Pro Ile Thr Lys Leu
                85                  90                  95

Thr Ala Pro Tyr Arg His Ala Gln Ile Val Glu Cys Lys Ala Ile Leu
            100                 105                 110

Thr Pro Thr Asp Leu Ala Val Ser Asn Pro Leu Thr Val Tyr Leu Ala
        115                 120                 125

Trp Val Pro Ala Asn Ser Pro Ala Thr Pro Thr Gln Ile Leu Arg Val
    130                 135                 140

Tyr Gly Gly Gln Ser Phe Val Leu Gly Gly Ala Ile Ser Ala Ala Lys
145                 150                 155                 160

Thr Ile Glu Val Pro Leu Asn Leu Asp Ser Val Asn Arg Met Leu Lys
                165                 170                 175

Asp Ser Val Thr Tyr Thr Asp Thr Pro Lys Leu Leu Ala Tyr Ser Arg
            180                 185                 190

Ala Pro Thr Asn Pro Ser Lys Ile Pro Thr Ala Ser Ile Gln Ile Ser
        195                 200                 205

Gly Arg Ile Arg Leu Ser Lys Pro Met Leu Ile Ala Asn
    210                 215                 220

<210> SEQ ID NO 8
<211> LENGTH: 666
<212> TYPE: DNA
<213> ORGANISM: Artificial
<220> FEATURE:
<223> OTHER INFORMATION: Synthetic

<400> SEQUENCE: 8

| | | | | |
|---|---|---|---|---|
| atgaacgaat | acatcgaaaa | agcgaacatc | accaccgatg | ataaaggtgg tagcggtccg | 60 |
| tatgccggtc | cgctggaacg | tcagaaaccg | ctgaaaggtg | gttctccgat ggagcgccaa | 120 |
| aagccattaa | aggtgaaagc | gaaagcgccg | ggtagcattc | tgagccagcc gaataccgaa | 180 |
| cagagcccgg | cgattgttct | gccgtttcag | tttgaagcga | ccaccttggg taccgctgaa | 240 |
| accgcagccc | aagtctctct | ccagactgcc | gaccccatta | ccaaactgac cgcccctac | 300 |

```
cgacatgctc agatcgtcga gtgcaaagct atcctcactc caactgatct tgctgtctcc   360
aatcccctca cagtctacct agcatgggtc cccgccaact cccctgccac tccgactcaa   420
atactgcgag tctacggcgg tcagtctttt gttcttggcg cgccatctc  agccgccaaa   480 accattgagg tcccccctcaa tcttgactct gtcaaccgca tgttgaaaga cagcgtgacc   540
tacactgaca cccccaagct ccttgcctac tcaagagccc ccaccaaccc ctcgaaaatc   600
ccaaccgcta gtattcagat cagcggtcgc attcggctct ccaagccaat gctgatagcc   660
aactaa                                                              666
```

```
<210> SEQ ID NO 9
<211> LENGTH: 219
<212> TYPE: PRT
<213> ORGANISM: Artificial
<220> FEATURE:
<223> OTHER INFORMATION: Synthetic

<400> SEQUENCE: 9
```

```
Met Arg Lys Thr Lys Leu Ala Pro Thr Val Ala His Gly Val Phe Gly
 1               5                  10                  15

Gly Ser Met Arg Lys Thr Lys Leu Ala Pro Thr Val Ala His Gly Val
             20                  25                  30

Phe Gly Gly Ser Met Arg Lys Thr Lys Leu Ala Pro Thr Val Ala His
         35                  40                  45

Gly Val Phe Leu Ser Gln Pro Asn Thr Glu Gln Ser Pro Ala Ile Val
     50                  55                  60

Leu Pro Phe Gln Phe Glu Ala Thr Thr Phe Gly Thr Ala Glu Thr Ala
 65                  70                  75                  80

Ala Gln Val Ser Leu Gln Thr Ala Asp Pro Ile Thr Lys Leu Thr Ala
                 85                  90                  95

Pro Tyr Arg His Ala Gln Ile Val Glu Cys Lys Ala Ile Leu Thr Pro
            100                 105                 110

Thr Asp Leu Ala Val Ser Asn Pro Leu Thr Val Tyr Leu Ala Trp Val
        115                 120                 125

Pro Ala Asn Ser Pro Ala Thr Pro Thr Gln Ile Leu Arg Val Tyr Gly
    130                 135                 140

Gly Gln Ser Phe Val Leu Gly Gly Ala Ile Ser Ala Ala Lys Thr Ile
145                 150                 155                 160

Glu Val Pro Leu Asn Leu Asp Ser Val Asn Arg Met Leu Lys Asp Ser
                165                 170                 175

Val Thr Tyr Thr Asp Thr Pro Lys Leu Leu Ala Tyr Ser Arg Ala Pro
            180                 185                 190

Thr Asn Pro Ser Lys Ile Pro Thr Ala Ser Ile Gln Ile Ser Gly Arg
        195                 200                 205

Ile Arg Leu Ser Lys Pro Met Leu Ile Ala Asn
    210                 215
```

```
<210> SEQ ID NO 10
<211> LENGTH: 660
<212> TYPE: DNA
<213> ORGANISM: Artificial
<220> FEATURE:
<223> OTHER INFORMATION: Synthetic

<400> SEQUENCE: 10
atgcgtaaaa ccaaactggc gccgaccgtg gcccatggcg tgtttggcgg cagcatgcgc    60
aaaacgaaac tggcccccgac ggttgctcac ggtgtgttcg gcggctcgat gcgcaaaacc   120
```

```
aaactggcac cgacggtggc acacggcgtt tttctgagcc agccgaacac cgaacagagc    180
ccggcgattg tgctgccgtt tcagtttgaa gcgaccacct tggtaccgc tgaaaccgca    240 gcccaagtct ctctccagac tgccgacccc attaccaaac tgaccgcccc ctaccgacat    300
gctcagatcg tcgagtgcaa agctatcctc actccaactg atcttgctgt ctccaatccc    360
ctcacagtct acctagcatg ggtccccgcc aactcccctg ccactccgac tcaaatactg    420
cgagtctacg gcggtcagtc ttttgttctt ggcggcgcca tctcagccgc caaaaccatt    480
gaggtccccc tcaatcttga ctctgtcaac cgcatgttga agacagcgt gacctacact    540 gacacccca gctccttgc ctactcaaga gcccccacca cccctcgaa atcccaacc    600 gctagtattc agatcagcgg tcgcattcgg ctctccaagc caatgctgat agccaactaa    660
```

<210> SEQ ID NO 11
<211> LENGTH: 217
<212> TYPE: PRT
<213> ORGANISM: Artificial
<220> FEATURE:
<223> OTHER INFORMATION: Synthetic

<400> SEQUENCE: 11

Met Asn Glu Tyr Ile Glu Lys Ala Asn Ile Thr Thr Asp Asp Lys Gly
1               5                   10                  15

Gly Ser Gly Pro Tyr Ala Gly Pro Leu Glu Arg Gln Lys Pro Leu Lys
            20                  25                  30

Val Lys Ala Lys Ala Gly Gly Ser Met Arg Lys Thr Lys Leu Ala Pro
        35                  40                  45

Thr Val Ala His Gly Val Phe Glu Gln Ser Pro Ala Ile Val Leu Pro
    50                  55                  60

Phe Gln Phe Glu Ala Thr Thr Phe Gly Thr Ala Glu Thr Ala Ala Gln
65                  70                  75                  80

Val Ser Leu Gln Thr Ala Asp Pro Ile Thr Lys Leu Thr Ala Pro Tyr
                85                  90                  95

Arg His Ala Gln Ile Val Glu Cys Lys Ala Ile Leu Thr Pro Thr Asp
            100                 105                 110

Leu Ala Val Ser Asn Pro Leu Thr Val Tyr Leu Ala Trp Val Pro Ala
        115                 120                 125

Asn Ser Pro Ala Thr Pro Thr Gln Ile Leu Arg Val Tyr Gly Gly Gln
    130                 135                 140

Ser Phe Val Leu Gly Gly Ala Ile Ser Ala Ala Lys Thr Ile Glu Val
145                 150                 155                 160

Pro Leu Asn Leu Asp Ser Val Asn Arg Met Leu Lys Asp Ser Val Thr
                165                 170                 175

Tyr Thr Asp Thr Pro Lys Leu Leu Ala Tyr Ser Arg Ala Pro Thr Asn
            180                 185                 190

Pro Ser Lys Ile Pro Thr Ala Ser Ile Gln Ile Ser Gly Arg Ile Arg
        195                 200                 205

Leu Ser Lys Pro Met Leu Ile Ala Asn
    210                 215

<210> SEQ ID NO 12
<211> LENGTH: 654
<212> TYPE: DNA
<213> ORGANISM: Artificial
<220> FEATURE:
<223> OTHER INFORMATION: Synthetic

<400> SEQUENCE: 12

```
atgaacgaat acatcgaaaa agcgaacatt accaccgatg ataaaggcgg cagcggcccg    60
tatgccggtc cgctggaacg tcagaaaccg ctgaaagtga aagcgaaagc gggcggtagc   120
atgcgtaaaa ccaaactggc gccgaccgtg gcccatggcg tgtttgaaca gagcccggcg   180
attgtgctgc cgtttcagtt tgaagcgacc acctttggta ccgctgaaac cgcagcccaa   240
gtctctctcc agactgccga ccccattacc aaactgaccg cccccctaccg acatgctcag   300
atcgtcgagt gcaaagctat cctcactcca actgatcttg ctgtctccaa tcccctcaca   360
gtctacctag catgggtccc cgccaactcc cctgccactc cgactcaaat actgcgagtc   420
tacggcggtc agtcttttgt tcttggcggc gccatctcag ccgccaaaac cattgaggtc   480
cccctcaatc ttgactctgt caaccgcatg ttgaaagaca gcgtgaccta cactgacacc   540
cccaagctcc ttgcctactc aagagccccc accaacccct cgaaaatccc aaccgctagt   600
attcagatca gcggtcgcat tcggctctcc aagccaatgc tgatagccaa ctaa         654
```

<210> SEQ ID NO 13
<211> LENGTH: 219
<212> TYPE: PRT
<213> ORGANISM: Artificial
<220> FEATURE:
<223> OTHER INFORMATION: Synthetic

<400> SEQUENCE: 13

```
Met Glu Thr Gln Ile Gln Arg Arg Gln His Thr Asp Val Ser Phe Ile
1               5                   10                  15

Met Asp Arg Phe Val Gly Gly Ser Lys Val Thr Pro Gln Asn Gln Ile
            20                  25                  30

Asn Ile Leu Asp Leu Met Gln Val Pro Ser His Thr Gly Gly Ser Pro
        35                  40                  45

Gly Ser Ile Leu Ser Gln Pro Asn Thr Glu Gln Ser Pro Ala Ile Val
    50                  55                  60

Leu Pro Phe Gln Phe Glu Ala Thr Thr Phe Gly Thr Ala Glu Thr Ala
65                  70                  75                  80

Ala Gln Val Ser Leu Gln Thr Ala Asp Pro Ile Thr Lys Leu Thr Ala
                85                  90                  95

Pro Tyr Arg His Ala Gln Ile Val Glu Cys Lys Ala Ile Leu Thr Pro
            100                 105                 110

Thr Asp Leu Ala Val Ser Asn Pro Leu Thr Val Tyr Leu Ala Trp Val
        115                 120                 125

Pro Ala Asn Ser Pro Ala Thr Pro Thr Gln Ile Leu Arg Val Tyr Gly
    130                 135                 140

Gly Gln Ser Phe Val Leu Gly Gly Ala Ile Ser Ala Ala Lys Thr Ile
145                 150                 155                 160

Glu Val Pro Leu Asn Leu Asp Ser Val Asn Arg Met Leu Lys Asp Ser
                165                 170                 175

Val Thr Tyr Thr Asp Thr Pro Lys Leu Leu Ala Tyr Ser Arg Ala Pro
            180                 185                 190

Thr Asn Pro Ser Lys Ile Pro Thr Ala Ser Ile Gln Ile Ser Gly Arg
        195                 200                 205

Ile Arg Leu Ser Lys Pro Met Leu Ile Ala Asn
    210                 215
```

<210> SEQ ID NO 14
<211> LENGTH: 660
<212> TYPE: DNA
<213> ORGANISM: Artificial
<220> FEATURE:
<223> OTHER INFORMATION: Synthetic

<400> SEQUENCE: 14

```
atggaaaccc agattcagcg tcgtcagcat accgatgtga gctttatcat ggatcgtttt      60
gtgggcggca gcaaagtgac cccgcagaac cagattaaca ttctggatct gatgcaggtt     120
ccgagccata ccggtggtag cccgggcagc attctgagcc agccgaacac cgaacagagc     180
ccggcgattg tgctgccgtt tcagtttgaa gcgaccacct ttggtaccgc tgaaaccgca     240
gcccaagtct ctctccagac tgccgacccc attaccaaac tgaccgcccc ctaccgacat     300
gctcagatcg tcgagtgcaa agctatcctc actccaactg atcttgctgt ctccaatccc     360
ctcacagtct acctagcatg gtccccgcc aactcccctg ccactccgac tcaaatactg     420
cgagtctacg gcggtcagtc ttttgttctt ggcggcgcca tctcagccgc caaaaccatt     480
gaggtccccc tcaatcttga ctctgtcaac cgcatgttga agacagcgt gacctacact     540 gacacccca agctccttgc ctactcaaga gcccccacca cccctcgaa atcccaacc      600 gctagtattc agatcagcgg tcgcattcgg ctctccaagc caatgctgat agccaactaa     660
```

<210> SEQ ID NO 15
<211> LENGTH: 229
<212> TYPE: PRT
<213> ORGANISM: Artificial
<220> FEATURE:
<223> OTHER INFORMATION: Synthetic

<400> SEQUENCE: 15

```
Met Arg Tyr Ser Arg Asn Ala Val Pro Asn Leu Arg Gly Asp Leu Gln
1               5                   10                  15

Val Leu Ala Gln Lys Val Ala Arg Thr Leu Pro Gly Gly Ser Arg Tyr
            20                  25                  30

Ser Arg Asn Ala Val Pro Asn Leu Arg Gly Asp Leu Gln Val Leu Ala
        35                  40                  45

Gln Lys Val Ala Arg Thr Leu Pro Gly Gly Ser Pro Asn Leu Arg Gly
    50                  55                  60

Asp Leu Gln Val Leu Ser Pro Ala Ile Val Leu Pro Phe Gln Phe Glu
65                  70                  75                  80

Ala Thr Thr Phe Gly Thr Ala Glu Thr Ala Gln Val Ser Leu Gln
                85                  90                  95

Thr Ala Asp Pro Ile Thr Lys Leu Thr Ala Pro Tyr Arg His Ala Gln
            100                 105                 110

Ile Val Glu Cys Lys Ala Ile Leu Thr Pro Thr Asp Leu Ala Val Ser
        115                 120                 125

Asn Pro Leu Thr Val Tyr Leu Ala Trp Val Pro Ala Asn Ser Pro Ala
    130                 135                 140

Thr Pro Thr Gln Ile Leu Arg Val Tyr Gly Gly Gln Ser Phe Val Leu
145                 150                 155                 160

Gly Gly Ala Ile Ser Ala Ala Lys Thr Ile Glu Val Pro Leu Asn Leu
                165                 170                 175

Asp Ser Val Asn Arg Met Leu Lys Asp Ser Val Thr Tyr Thr Asp Thr
            180                 185                 190

Pro Lys Leu Leu Ala Tyr Ser Arg Ala Pro Thr Asn Pro Ser Lys Ile
        195                 200                 205
```

```
Pro Thr Ala Ser Ile Gln Ile Ser Gly Arg Ile Arg Leu Ser Lys Pro
    210                 215                 220

Met Leu Ile Ala Asn
225

<210> SEQ ID NO 16
<211> LENGTH: 690
<212> TYPE: DNA
<213> ORGANISM: Artificial
<220> FEATURE:
<223> OTHER INFORMATION: Synthetic

<400> SEQUENCE: 16
atgcgttata gccgtaacgc cgtgccgaac ctgcgtggtg atctgcaggt gctggcccag      60
aaagtggcac gtaccctgcc gggtggcagc cgctattctc gtaatgccgt tccgaatctg    120
cgcggcgacc tgcaagttct ggcacaaaaa gttgcccgta cgctgccggg cggtagcccg    180
aatctgcgtg gcgatctgca ggttctgtct ccggcgattg tgctgccgtt tcagtttgaa    240
gcgaccacct ttggtaccgc tgaaaccgca gcccaagtct ctctccagac tgccgacccc    300
attaccaaac tgaccgcccc ctaccgacat gctcagatcg tcgagtgcaa agctatcctc    360
actccaactg atcttgctgt ctccaatccc ctcacagtct acctagcatg ggtccccgcc    420
aactcccctg ccactccgac tcaaatactg cgagtctacg gcggtcagtc ttttgttctt    480
ggcggcgcca tctcagccgc caaaaccatt gaggtccccc tcaatcttga ctctgtcaac    540
cgcatgttga agacagcgt gacctacact gacaccccca agctccttgc ctactcaaga    600
gcccccacca cccctcgaa atcccaacc gctagtattc agatcagcgg tcgcattcgg    660
ctctccaagc caatgctgat agccaactaa                                    690

<210> SEQ ID NO 17
<211> LENGTH: 220
<212> TYPE: PRT
<213> ORGANISM: Artificial
<220> FEATURE:
<223> OTHER INFORMATION: Synthetic

<400> SEQUENCE: 17

Met Arg His Lys Gln Lys Ile Val Ala Pro Val Lys Gln Thr Leu Gly
1               5                   10                  15

Gly Ser Arg His Lys Gln Lys Ile Val Ala Pro Val Lys Gln Thr Leu
            20                  25                  30

Gly Gly Ser Arg His Lys Gln Lys Ile Val Ala Pro Val Lys Gln Thr
        35                  40                  45

Leu Gly Gly Ser Leu Ser Gln Pro Asn Thr Glu Gln Ser Pro Ala Ile
    50                  55                  60

Val Leu Pro Phe Gln Phe Glu Ala Thr Thr Phe Gly Thr Ala Glu Thr
65                  70                  75                  80

Ala Ala Gln Val Ser Leu Gln Thr Ala Asp Pro Ile Thr Lys Leu Thr
                85                  90                  95

Ala Pro Tyr Arg His Ala Gln Ile Val Glu Cys Lys Ala Ile Leu Thr
            100                 105                 110

Pro Thr Asp Leu Ala Val Ser Asn Pro Leu Thr Val Tyr Leu Ala Trp
        115                 120                 125

Val Pro Ala Asn Ser Pro Ala Thr Pro Thr Gln Ile Leu Arg Val Tyr
    130                 135                 140

Gly Gly Gln Ser Phe Val Leu Gly Gly Ala Ile Ser Ala Ala Lys Thr
145                 150                 155                 160
```

```
Ile Glu Val Pro Leu Asn Leu Asp Ser Val Asn Arg Met Leu Lys Asp
                165                 170                 175

Ser Val Thr Tyr Thr Asp Thr Pro Lys Leu Leu Ala Tyr Ser Arg Ala
            180                 185                 190

Pro Thr Asn Pro Ser Lys Ile Pro Thr Ala Ser Ile Gln Ile Ser Gly
        195                 200                 205

Arg Ile Arg Leu Ser Lys Pro Met Leu Ile Ala Asn
    210                 215                 220
```

<210> SEQ ID NO 18
<211> LENGTH: 663
<212> TYPE: DNA
<213> ORGANISM: Artificial
<220> FEATURE:
<223> OTHER INFORMATION: Synthetic

<400> SEQUENCE: 18

```
atgcgccata aacagaaaat tgtggcgccg gtgaaacaga ccctgggcgg cagccgtcac    60
aaacagaaaa tcgttgcccc ggttaaacaa acgctgggcg ttctcgtca taaacaaaaa    120
atcgtcgctc cggtcaaaca gaccctgggt ggtagcctga ccagccgaa caccgaacag    180
agcccggcga ttgtgctgcc gtttcagttt gaagcgacca cctttggtac cgctgaaacc   240
gcagcccaag tctctctcca gactgccgac cccattacca aactgaccgc ccctaccga    300
catgctcaga tcgtcgagtg caaagctatc ctcactccaa ctgatcttgc tgtctccaat   360
cccctcacag tctacctagc atgggtcccc gccaactccc ctgccactcc gactcaaata   420
ctgcgagtct acggcggtca gtcttttgtt cttggcggcg ccatctcagc cgccaaaacc   480
attgaggtcc ccctcaatct tgactctgtc aaccgcatgt tgaaagacag cgtgacctac   540
actgacaccc ccaagctcct tgcctactca agagccccca ccaaccccct cgaaaatccca   600
accgctagta ttcagatcag cggtcgcatt cggctctcca agccaatgct gatagccaac   660
taa                                                                 663
```

<210> SEQ ID NO 19
<211> LENGTH: 227
<212> TYPE: PRT
<213> ORGANISM: Artificial
<220> FEATURE:
<223> OTHER INFORMATION: Synthetic

<400> SEQUENCE: 19

```
Met Glu His Trp Ser Tyr Gly Leu Arg Pro Gly Gly Gly Ser Glu His
1               5                   10                  15

Trp Ser Tyr Gly Leu Arg Pro Gly Gly Gly Ser Glu His Trp Ser Tyr
            20                  25                  30

Gly Leu Arg Pro Gly Gly Gly Ser Glu His Trp Ser Tyr Gly Leu Arg
        35                  40                  45

Pro Gly Gly Gly Ser Glu His Trp Ser Tyr Gly Leu Arg Pro Gly Gly
    50                  55                  60

Gly Ser Gln Ser Pro Ala Ile Val Leu Pro Phe Gln Phe Glu Ala Thr
65                  70                  75                  80

Thr Phe Gly Thr Ala Glu Thr Ala Ala Gln Val Ser Leu Gln Thr Ala
                85                  90                  95

Asp Pro Ile Thr Lys Leu Thr Ala Pro Tyr Arg His Ala Gln Ile Val
            100                 105                 110

Glu Cys Lys Ala Ile Leu Thr Pro Thr Asp Leu Ala Val Ser Asn Pro
        115                 120                 125
```

```
Leu Thr Val Tyr Leu Ala Trp Val Pro Ala Asn Ser Pro Ala Thr Pro
    130                 135                 140
Thr Gln Ile Leu Arg Val Tyr Gly Gly Gln Ser Phe Val Leu Gly Gly
145                 150                 155                 160
Ala Ile Ser Ala Ala Lys Thr Ile Glu Val Pro Leu Asn Leu Asp Ser
                165                 170                 175
Val Asn Arg Met Leu Lys Asp Ser Val Thr Tyr Thr Asp Thr Pro Lys
            180                 185                 190
Leu Leu Ala Tyr Ser Arg Ala Pro Thr Asn Pro Ser Lys Ile Pro Thr
                195                 200                 205
Ala Ser Ile Gln Ile Ser Gly Arg Ile Arg Leu Ser Lys Pro Met Leu
    210                 215                 220
Ile Ala Asn
225

<210> SEQ ID NO 20
<211> LENGTH: 684
<212> TYPE: DNA
<213> ORGANISM: Artificial
<220> FEATURE:
<223> OTHER INFORMATION: Synthetic

<400> SEQUENCE: 20
atggaacatt ggagctatgg cctgcgtccg ggcggtggca gcgaacattg gtcttacggt      60
ctgcgtccgg gtggcggctc tgaacactgg tcctatggcc tgcgtccggg tggcggttcc     120
gaacattgga gctacggtct gcgtccgggt ggtggtagcg aacactggag ttatggcctg     180
cgtccgggtg gtggtagtca gagcccggcg attgtgctgc cgtttcagtt tgaagcgacc     240
acctttggta ccgctgaaac cgcagcccaa gtctctctcc agactgccga ccccattacc     300
aaactgaccg cccctaccg acatgctcag atcgtcgagt gcaaagctat cctcactcca     360
actgatcttg ctgtctccaa tcccctcaca gtctacctag catgggtccc cgccaactcc     420
cctgccactc cgactcaaat actgcgagtc tacggcggtc agtcttttgt tcttggcggc     480
gccatctcag ccgccaaaac cattgaggtc cccctcaatc ttgactctgt caaccgcatg     540
ttgaaagaca gcgtgaccta cactgacacc cccaagctcc ttgcctactc aagagccccc     600
accaacccct cgaaaatccc aaccgctagt attcagatca gcggtcgcat tcggctctcc     660
aagccaatgc tgatagccaa ctaa                                            684

<210> SEQ ID NO 21
<211> LENGTH: 227
<212> TYPE: PRT
<213> ORGANISM: Artificial
<220> FEATURE:
<223> OTHER INFORMATION: Synthetic

<400> SEQUENCE: 21

Met Thr Ala Ala Gln Ile Thr Ala Gly Ile Ala Leu His Gln Ser Asn
1               5                   10                  15
Leu Asn Gly Gly Ser Glu His Trp Ser Tyr Gly Leu Arg Pro Gly Gly
            20                  25                  30
Gly Ser Thr Ala Ala Gln Ile Thr Ala Gly Ile Ala Leu His Gln Ser
        35                  40                  45
Asn Leu Asn Gly Gly Ser Glu His Trp Ser Tyr Gly Leu Arg Pro Gly
    50                  55                  60
Gly Gly Ser Ser Pro Ala Ile Val Leu Pro Phe Gln Phe Glu Ala Thr
65                  70                  75                  80
```

Thr Phe Gly Thr Ala Glu Thr Ala Ala Gln Val Ser Leu Gln Thr Ala
                85                  90                  95

Asp Pro Ile Thr Lys Leu Thr Ala Pro Tyr Arg His Ala Gln Ile Val
            100                 105                 110

Glu Cys Lys Ala Ile Leu Thr Pro Thr Asp Leu Ala Val Ser Asn Pro
        115                 120                 125

Leu Thr Val Tyr Leu Ala Trp Val Pro Ala Asn Ser Pro Ala Thr Pro
    130                 135                 140

Thr Gln Ile Leu Arg Val Tyr Gly Gly Gln Ser Phe Val Leu Gly Gly
145                 150                 155                 160

Ala Ile Ser Ala Ala Lys Thr Ile Glu Val Pro Leu Asn Leu Asp Ser
                165                 170                 175

Val Asn Arg Met Leu Lys Asp Ser Val Thr Tyr Thr Asp Thr Pro Lys
            180                 185                 190

Leu Leu Ala Tyr Ser Arg Ala Pro Thr Asn Pro Ser Lys Ile Pro Thr
        195                 200                 205

Ala Ser Ile Gln Ile Ser Gly Arg Ile Arg Leu Ser Lys Pro Met Leu
    210                 215                 220

Ile Ala Asn
225

<210> SEQ ID NO 22
<211> LENGTH: 684
<212> TYPE: DNA
<213> ORGANISM: Artificial
<220> FEATURE:
<223> OTHER INFORMATION: Synthetic

<400> SEQUENCE: 22
atgaccgccg ctcagattac cgccggcatt gcgctgcatc agagcaacct gaacggcggc      60
agcgaacatt ggagctatgg cctgcgtccg ggtggtggta gcacggcggc acagatcacc     120
gctggtatcg ccctgcatca gtctaacctg aatggcggtt ctgaacattg gtcttacggt     180
ctgcgtccgg gcggtggcag ctctccggcg attgtgctgc cgtttcagtt tgaagcgacc     240
acctttggta ccgctgaaac cgcagcccaa gtctctctcc agactgccga ccccattacc     300
aaactgaccg cccctaccg acatgctcag atcgtcgagt gcaaagctat cctcactcca     360
actgatcttg ctgtctccaa tcccctcaca gtctacctag catgggtccc cgccaactcc     420
cctgccactc cgactcaaat actgcgagtc tacggcggtc agtcttttgt tcttggcggc     480
gccatctcag ccgccaaaac cattgaggtc cccctcaatc ttgactctgt caaccgcatg     540
ttgaaagaca gcgtgaccta cactgacacc cccaagctcc ttgcctactc aagagccccc     600
accaacccct cgaaaatccc aaccgctagt attcagatca gcggtcgcat tcggctctcc     660
aagccaatgc tgatagccaa ctaa                                             684

<210> SEQ ID NO 23
<211> LENGTH: 222
<212> TYPE: PRT
<213> ORGANISM: Artificial
<220> FEATURE:
<223> OTHER INFORMATION: Synthetic

<400> SEQUENCE: 23

Met Thr Ala Ala Gln Ile Thr Ala Gly Ile Ala Leu His Gln Ser Asn
1               5                   10                  15

Leu Asn Gly Gly Ser Glu His Trp Ser Tyr Gly Leu Arg Pro Gly Gly
            20                  25                  30

Gly Ser Glu His Trp Ser Tyr Gly Leu Arg Pro Gly Gly Gly Ser Glu
            35                  40                  45

His Trp Ser Tyr Gly Leu Arg Pro Gly Gly Gly Ser Glu Gln Ser Pro
    50                  55                  60

Ala Ile Val Leu Pro Phe Gln Phe Glu Ala Thr Thr Phe Gly Thr Ala
65                  70                  75                  80

Glu Thr Ala Ala Gln Val Ser Leu Gln Thr Ala Asp Pro Ile Thr Lys
                85                  90                  95

Leu Thr Ala Pro Tyr Arg His Ala Gln Ile Val Glu Cys Lys Ala Ile
                100                 105                 110

Leu Thr Pro Thr Asp Leu Ala Val Ser Asn Pro Leu Thr Val Tyr Leu
                115                 120                 125

Ala Trp Val Pro Ala Asn Ser Pro Ala Thr Pro Thr Gln Ile Leu Arg
130                 135                 140

Val Tyr Gly Gly Gln Ser Phe Val Leu Gly Gly Ala Ile Ser Ala Ala
145                 150                 155                 160

Lys Thr Ile Glu Val Pro Leu Asn Leu Asp Ser Val Asn Arg Met Leu
                165                 170                 175

Lys Asp Ser Val Thr Tyr Thr Asp Thr Pro Lys Leu Leu Ala Tyr Ser
                180                 185                 190

Arg Ala Pro Thr Asn Pro Ser Lys Ile Pro Thr Ala Ser Ile Gln Ile
                195                 200                 205

Ser Gly Arg Ile Arg Leu Ser Lys Pro Met Leu Ile Ala Asn
                210                 215                 220

<210> SEQ ID NO 24
<211> LENGTH: 669
<212> TYPE: DNA
<213> ORGANISM: Artificial
<220> FEATURE:
<223> OTHER INFORMATION: Synthetic

<400> SEQUENCE: 24
atgaccgccg ctcagattac cgccggcatt gcgctgcatc agagcaacct gaacggcggc      60
agcgaacatt ggagctatgg cctgcgtccg ggcggtggca gcgaacactg gtcttacggt     120
ctgcgtccgg gtggcggctc tgaacattgg tcgtatggcc tgcgtccggg tggcggtagt     180
gaacagagcc cggcgattgt gctgccgttt cagtttgaag cgaccacctt tggtaccgct     240
gaaaccgcag cccaagtctc tctccagact gccgacccca ttaccaaact gaccgccccc     300
taccgacatg ctcagatcgt cgagtgcaaa gctatcctca ctccaactga tcttgctgtc     360
tccaatcccc tcacagtcta cctagcatgg gtccccgcca actccctgc cactccgact      420 caaatactgc gagtctacgg cggtcagtct tttgttcttg gcggcgccat ctcagccgcc     480
aaaaccattg aggtccccct caatcttgac tctgtcaacc gcatgttgaa agacagcgtg     540
acctacactg acaccccaa gctccttgcc tactcaagag cccccaccaa ccctcgaaa       600 atcccaaccg ctagtattca gatcagcggt cgcattcggc tctccaagcc aatgctgata     660
gccaactaa                                                             669

<210> SEQ ID NO 25
<211> LENGTH: 227
<212> TYPE: PRT
<213> ORGANISM: Artificial
<220> FEATURE:
<223> OTHER INFORMATION: Synthetic

<400> SEQUENCE: 25

```
Met Ser Asp Gly Ala Val Gln Pro Asp Gly Gln Pro Ala Val Arg
1               5                   10                  15

Asn Glu Arg Gly Gly Ser Lys Thr Ala Val Asn Gly Asn Met Ala Leu
                20                  25                  30

Asp Asp Thr His Ala Gly Gly Ser Ala Leu Gly Leu Pro Pro Phe Leu
            35                  40                  45

Asn Ser Leu Pro Gln Ser Glu Gly Gly Thr Asn Phe Gly Tyr Ile Gly
        50                  55                  60

Val Gln Gly Gly Ser Ala Ile Val Leu Pro Phe Gln Phe Glu Ala Thr
65                  70                  75                  80

Thr Phe Gly Thr Ala Glu Thr Ala Ala Gln Val Ser Leu Gln Thr Ala
                85                  90                  95

Asp Pro Ile Thr Lys Leu Thr Ala Pro Tyr Arg His Ala Gln Ile Val
            100                 105                 110

Glu Cys Lys Ala Ile Leu Thr Pro Thr Asp Leu Ala Val Ser Asn Pro
        115                 120                 125

Leu Thr Val Tyr Leu Ala Trp Val Pro Ala Asn Ser Pro Ala Thr Pro
130                 135                 140

Thr Gln Ile Leu Arg Val Tyr Gly Gly Gln Ser Phe Val Leu Gly Gly
145                 150                 155                 160

Ala Ile Ser Ala Ala Lys Thr Ile Glu Val Pro Leu Asn Leu Asp Ser
                165                 170                 175

Val Asn Arg Met Leu Lys Asp Ser Val Thr Tyr Thr Asp Thr Pro Lys
            180                 185                 190

Leu Leu Ala Tyr Ser Arg Ala Pro Thr Asn Pro Ser Lys Ile Pro Thr
        195                 200                 205

Ala Ser Ile Gln Ile Ser Gly Arg Ile Arg Leu Ser Lys Pro Met Leu
    210                 215                 220

Ile Ala Asn
225
```

<210> SEQ ID NO 26
<211> LENGTH: 684
<212> TYPE: DNA
<213> ORGANISM: Artificial
<220> FEATURE:
<223> OTHER INFORMATION: Synthetic

<400> SEQUENCE: 26

```
atgagcgatg gcgcggtgca gccggatggt ggtcagccgg cggtgcgtaa cgaacgtggc      60
ggcagcaaaa ccgcggtgaa cggcaacatg gcgctggatg ataccatgc gggcggtagc     120
gcgctgggtc tgccgccgtt tctgaacagc ctgccgcaga gcgaaggcgg caccaacttt     180
ggctatattg gcgtgcaggg cggcagcgcg attgtgctgc cgtttcagtt tgaagcgacc     240
acctttggta ccgctgaaac cgcagcccaa gtctctctcc agactgccga ccccattacc     300
aaactgaccg cccctaccg acatgctcag atcgtcgagt gcaaagctat cctcactcca     360
actgatcttg ctgtctccaa tcccctcaca gtctacctag catgggtccc cgccaactcc     420
cctgccactc cgactcaaat actgcgagtc tacggcggtc agtcttttgt tcttggcggc     480
gccatctcag ccgccaaaac cattgaggtc cccctcaatc ttgactctgt caaccgcatg     540
ttgaaagaca gcgtgaccta cactgacacc cccaagctcc ttgcctactc aagagccccc     600
```

```
accaacccct cgaaaatccc aaccgctagt attcagatca gcggtcgcat tcggctctcc    660
aagccaatgc tgatagccaa ctaa                                           684
```

<210> SEQ ID NO 27
<211> LENGTH: 223
<212> TYPE: PRT
<213> ORGANISM: Artificial
<220> FEATURE:
<223> OTHER INFORMATION: Synthetic

<400> SEQUENCE: 27

```
Met Thr Ala Ala Gln Ile Thr Ala Gly Ile Ala Leu His Gln Ser Asn
1               5                   10                  15

Leu Asn Gly Gly Ser Met Ser Asp Gly Ala Val Gln Pro Asp Gly Gly
            20                  25                  30

Gln Pro Ala Val Arg Asn Glu Arg Ala Thr Gly Gly Ser Thr Ala Ala
        35                  40                  45

Gln Ile Thr Ala Gly Ile Ala Leu His Gln Ser Asn Leu Asn Gly Gly
    50                  55                  60

Ser Ala Ile Val Leu Pro Phe Gln Phe Glu Ala Thr Thr Phe Gly Thr
65                  70                  75                  80

Ala Glu Thr Ala Ala Gln Val Ser Leu Gln Thr Ala Asp Pro Ile Thr
                85                  90                  95

Lys Leu Thr Ala Pro Tyr Arg His Ala Gln Ile Val Glu Cys Lys Ala
            100                 105                 110

Ile Leu Thr Pro Thr Asp Leu Ala Val Ser Asn Pro Leu Thr Val Tyr
        115                 120                 125

Leu Ala Trp Val Pro Ala Asn Ser Pro Ala Thr Pro Thr Gln Ile Leu
    130                 135                 140

Arg Val Tyr Gly Gly Gln Ser Phe Val Leu Gly Gly Ala Ile Ser Ala
145                 150                 155                 160

Ala Lys Thr Ile Glu Val Pro Leu Asn Leu Asp Ser Val Asn Arg Met
                165                 170                 175

Leu Lys Asp Ser Val Thr Tyr Thr Asp Thr Pro Lys Leu Leu Ala Tyr
            180                 185                 190

Ser Arg Ala Pro Thr Asn Pro Ser Lys Ile Pro Thr Ala Ser Ile Gln
        195                 200                 205

Ile Ser Gly Arg Ile Arg Leu Ser Lys Pro Met Leu Ile Ala Asn
    210                 215                 220
```

<210> SEQ ID NO 28
<211> LENGTH: 672
<212> TYPE: DNA
<213> ORGANISM: Artificial
<220> FEATURE:
<223> OTHER INFORMATION: Synthetic

<400> SEQUENCE: 28

```
atgaccgcgg cgcagattac cgcgggcatc gcgctgcatc agtctaacct gaacggcggc    60
agcatgagcg atggtgcggt gcagccggat ggtggtcagc cggcggtgcg taacgaacgt   120
gcgaccggcg gtagcaccgc cgcccagatc accgccggta tcgccctgca ccagagcaat   180
ctgaatggtg gtagcgcgat tgtgctgccg tttcagtttg aagcgaccac ctttggtacc   240
gctgaaaccg cagcccaagt ctctctccag actgccgacc ccattaccaa actgaccgcc   300
ccctaccgac atgctcagat cgtcgagtgc aaagctatcc tcactccaac tgatcttgct   360
gtctccaatc ccctcacagt ctacctagca tgggtccccg ccaactcccc tgccactccg   420
```

-continued

```
actcaaatac tgcgagtcta cggcggtcag tcttttgttc ttggcggcgc catctcagcc      480
gccaaaacca ttgaggtccc cctcaatctt gactctgtca accgcatgtt gaaagacagc      540
gtgacctaca ctgacacccc caagctcctt gcctactcaa gagcccccac caacccctcg      600
aaaatcccaa ccgctagtat tcagatcagc ggtcgcattc ggctctccaa gccaatgctg      660
atagccaact aa                                                          672
```

<210> SEQ ID NO 29
<211> LENGTH: 223
<212> TYPE: PRT
<213> ORGANISM: Artificial
<220> FEATURE:
<223> OTHER INFORMATION: Synthetic

<400> SEQUENCE: 29

```
Met Thr Ala Ala Gln Ile Thr Ala Gly Ile Ala Leu His Gln Ser Asn
1               5                   10                  15

Leu Asn Gly Gly Ser Met Ser Asp Gly Ala Val Gln Pro Asp Gly Gly
            20                  25                  30

Gln Pro Ala Val Arg Asn Glu Arg Gly Gly Ser Met Ser Asp Gly Ala
        35                  40                  45

Val Gln Pro Asp Gly Gly Gln Pro Ala Val Arg Asn Glu Arg Gly Gly
    50                  55                  60

Ser Ala Ile Val Leu Pro Phe Gln Phe Glu Ala Thr Thr Phe Gly Thr
65                  70                  75                  80

Ala Glu Thr Ala Ala Gln Val Ser Leu Gln Thr Ala Asp Pro Ile Thr
                85                  90                  95

Lys Leu Thr Ala Pro Tyr Arg His Ala Gln Ile Val Glu Cys Lys Ala
            100                 105                 110

Ile Leu Thr Pro Thr Asp Leu Ala Val Ser Asn Pro Leu Thr Val Tyr
        115                 120                 125

Leu Ala Trp Val Pro Ala Asn Ser Pro Ala Thr Pro Thr Gln Ile Leu
    130                 135                 140

Arg Val Tyr Gly Gly Gln Ser Phe Val Leu Gly Gly Ala Ile Ser Ala
145                 150                 155                 160

Ala Lys Thr Ile Glu Val Pro Leu Asn Leu Asp Ser Val Asn Arg Met
                165                 170                 175

Leu Lys Asp Ser Val Thr Tyr Thr Asp Thr Pro Lys Leu Leu Ala Tyr
            180                 185                 190

Ser Arg Ala Pro Thr Asn Pro Ser Lys Ile Pro Thr Ala Ser Ile Gln
        195                 200                 205

Ile Ser Gly Arg Ile Arg Leu Ser Lys Pro Met Leu Ile Ala Asn
    210                 215                 220
```

<210> SEQ ID NO 30
<211> LENGTH: 672
<212> TYPE: DNA
<213> ORGANISM: Artificial
<220> FEATURE:
<223> OTHER INFORMATION: Synthetic

<400> SEQUENCE: 30

```
atgaccgcgg cgcagattac cgcgggcatt gcgctgcatc agagcaacct gaacggtggc      60
agtatgtctg acggtgcggt gcagccggat ggtggtcaac cggcggtgcg taacgagcgt      120
ggcggtagca tgagcgatgg cgccgttcag ccggatggcg ccagccggc cgttcgcaat      180 gaacgtggtg gcagcgcgat tgtgctgccg tttcagtttg aagcgaccac ctttggtacc      240
```

```
gctgaaaccg cagcccaagt ctctctccag actgccgacc ccattaccaa actgaccgcc    300
ccctaccgac atgctcagat cgtcgagtgc aaagctatcc tcactccaac tgatcttgct    360
gtctccaatc ccctcacagt ctacctagca tgggtccccg ccaactcccc tgccactccg    420
actcaaatac tgcgagtcta cggcggtcag tcttttgttc ttggcggcgc catctcagcc    480
gccaaaacca ttgaggtccc cctcaatctt gactctgtca accgcatgtt gaaagacagc    540
gtgacctaca ctgacacccc caagctcctt gcctactcaa gagcccccac caaccccttcg    600 aaaatcccaa ccgctagtat tcagatcagc ggtcgcattc ggctctccaa gccaatgctg    660
atagccaact aa                                                        672
```

<210> SEQ ID NO 31
<211> LENGTH: 229
<212> TYPE: PRT
<213> ORGANISM: Artificial
<220> FEATURE:
<223> OTHER INFORMATION: Synthetic

<400> SEQUENCE: 31

```
Met Thr Ala Ala Gln Ile Thr Ala Gly Ile Ala Leu His Gln Ser Asn
1               5                   10                  15

Leu Asn Gly Gly Ser Lys Thr Ala Val Asn Gly Asn Met Ala Leu Asp
            20                  25                  30

Asp Thr His Ala Gln Gly Gly Ser Arg Ala Leu Gly Leu Pro Pro Phe
        35                  40                  45

Leu Asn Ser Leu Pro Gln Ser Glu Gly Gly Thr Asn Phe Gly Tyr Ile
    50                  55                  60

Gly Val Gln Gln Gly Gly Ser Ala Ile Val Leu Pro Phe Gln Phe Glu
65                  70                  75                  80

Ala Thr Thr Phe Gly Thr Ala Glu Thr Ala Ala Gln Val Ser Leu Gln
                85                  90                  95

Thr Ala Asp Pro Ile Thr Lys Leu Thr Ala Pro Tyr Arg His Ala Gln
            100                 105                 110

Ile Val Glu Cys Lys Ala Ile Leu Thr Pro Thr Asp Leu Ala Val Ser
        115                 120                 125

Asn Pro Leu Thr Val Tyr Leu Ala Trp Val Pro Ala Asn Ser Pro Ala
    130                 135                 140

Thr Pro Thr Gln Ile Leu Arg Val Tyr Gly Gly Gln Ser Phe Val Leu
145                 150                 155                 160

Gly Gly Ala Ile Ser Ala Ala Lys Thr Ile Glu Val Pro Leu Asn Leu
                165                 170                 175

Asp Ser Val Asn Arg Met Leu Lys Asp Ser Val Thr Tyr Thr Asp Thr
            180                 185                 190

Pro Lys Leu Leu Ala Tyr Ser Arg Ala Pro Thr Asn Pro Ser Lys Ile
        195                 200                 205

Pro Thr Ala Ser Ile Gln Ile Ser Gly Arg Ile Arg Leu Ser Lys Pro
    210                 215                 220

Met Leu Ile Ala Asn
225
```

<210> SEQ ID NO 32
<211> LENGTH: 690
<212> TYPE: DNA
<213> ORGANISM: Artificial
<220> FEATURE:
<223> OTHER INFORMATION: Synthetic -continued

<400> SEQUENCE: 32

```
atgacagcag ctcagataac tgcgggtatc gcattgcatc agtcaaactt gaatggaggt    60
tcgaaaactg cagttaacgg aaacatggct ttagatgata ctcatgcaca aggaggttcg   120
agagcattgg gcttaccacc atttctaaat tctttgcctc aatctgaagg aggtactaac   180
tttggttata taggagttca acaaggaggt tcggccatag ttctcccttt tcagtttgaa   240
gccactactt tcggtaccgc tgaaaccgca gcccaagtct ctctccagac tgccgacccc   300
attaccaaac tgaccgcccc ctaccgacat gctcagatcg tcgagtgcaa agctatcctc   360
actccaactg atcttgctgt ctccaatccc ctcacagtct acctagcatg ggtccccgcc   420
aactcccctg ccactccgac tcaaatactg cgagtctacg gcggtcagtc ttttgttctt   480
ggcggcgcca tctcagccgc caaaaccatt gaggtccccc tcaatcttga ctctgtcaac   540
cgcatgttga agacagcgt gacctacact gacaccccca agctccttgc ctactcaaga   600
gcccccacca cccctcgaa aatcccaacc gctagtattc agatcagcgg tcgcattcgg   660
ctctccaagc caatgctgat agccaactaa                                   690
```

<210> SEQ ID NO 33
<211> LENGTH: 229
<212> TYPE: PRT
<213> ORGANISM: Artificial
<220> FEATURE:
<223> OTHER INFORMATION: Synthetic

<400> SEQUENCE: 33

```
Met Lys Thr Ala Val Asn Gly Asn Met Ala Leu Asp Asp Thr His Ala
 1               5                  10                  15

Gln Gly Gly Ser Arg Ala Leu Gly Leu Pro Pro Phe Leu Asn Ser Leu
            20                  25                  30

Pro Gln Ser Glu Gly Gly Thr Asn Phe Gly Tyr Ile Gly Val Gln Gln
        35                  40                  45

Gly Gly Ser Thr Ala Ala Gln Ile Thr Ala Gly Ile Ala Leu His Gln
    50                  55                  60

Ser Asn Leu Asn Gly Gly Ser Ala Ile Val Leu Pro Phe Gln Phe Glu
65                  70                  75                  80

Ala Thr Thr Phe Gly Thr Ala Glu Thr Ala Ala Gln Val Ser Leu Gln
                85                  90                  95

Thr Ala Asp Pro Ile Thr Lys Leu Thr Ala Pro Tyr Arg His Ala Gln
           100                 105                 110

Ile Val Glu Cys Lys Ala Ile Leu Thr Pro Thr Asp Leu Ala Val Ser
       115                 120                 125

Asn Pro Leu Thr Val Tyr Leu Ala Trp Val Pro Ala Asn Ser Pro Ala
   130                 135                 140

Thr Pro Thr Gln Ile Leu Arg Val Tyr Gly Gly Gln Ser Phe Val Leu
145                 150                 155                 160

Gly Gly Ala Ile Ser Ala Ala Lys Thr Ile Glu Val Pro Leu Asn Leu
               165                 170                 175

Asp Ser Val Asn Arg Met Leu Lys Asp Ser Val Thr Tyr Thr Asp Thr
           180                 185                 190

Pro Lys Leu Leu Ala Tyr Ser Arg Ala Pro Thr Asn Pro Ser Lys Ile
       195                 200                 205
```

```
Pro Thr Ala Ser Ile Gln Ile Ser Gly Arg Ile Arg Leu Ser Lys Pro
    210                 215                 220

Met Leu Ile Ala Asn
225

<210> SEQ ID NO 34
<211> LENGTH: 690
<212> TYPE: DNA
<213> ORGANISM: Artificial
<220> FEATURE:
<223> OTHER INFORMATION: Synthetic

<400> SEQUENCE: 34
atgaaaaccg cggtgaacgg caacatggcg ctggatgata cccatgcgca gggcggtagc      60
cgtgcgctgg gtctgccgcc gtttctgaac agcctgccgc agagcgaagg cggcaccaac     120
tttggctata ttggcgtgca gcagggtggt agcaccgcgg cgcagattac cgcgggcatt     180
gcgctgcatc agagcaacct gaacggcggc agcgcgattg tgctgccgtt tcagtttgaa     240
gcgaccacct ttggtaccgc tgaaaccgca gcccaagtct ctctccagac tgccgacccc     300
attaccaaac tgaccgcccc ctaccgacat gctcagatcg tcgagtgcaa agctatcctc     360
actccaactg atcttgctgt ctccaatccc ctcacagtct acctagcatg ggtccccgcc     420
aactcccctg ccactccgac tcaaatactg cgagtctacg gcggtcagtc ttttgttctt     480
ggcggcgcca tctcagccgc caaaaccatt gaggtccccc tcaatcttga ctctgtcaac     540
cgcatgttga agacagcgt gacctacact gacaccccca agctccttgc ctactcaaga     600
gcccccacca accccctcgaa aatcccaacc gctagtattc agatcagcgg tcgcattcgg     660
ctctccaagc caatgctgat agccaactaa                                      690
```